(12) United States Patent
Mahony et al.

(10) Patent No.: US 11,371,075 B2
(45) Date of Patent: Jun. 28, 2022

(54) FULLY INTEGRATED HAND-HELD DEVICE TO DETECT SPECIFIC NUCLEIC ACID SEQUENCES

(71) Applicant: ADVANCED THERANOSTICS INC., Oakville (CA)

(72) Inventors: James Mahony, Oakville (CA); Christopher Stone, Oakville (CA); Hao Chen, Oakville (CA); Mark Costa, Oakville (CA); Bernard Lim, Oakville (CA)

(73) Assignee: ADVANCED THERANOSTICS INC., Oakville (CA)

( * ) Notice: Subject to any disclaimer, the term of this patent is extended or adjusted under 35 U.S.C. 154(b) by 0 days.

(21) Appl. No.: 16/068,565

(22) PCT Filed: Jan. 9, 2017

(86) PCT No.: PCT/CA2017/000001
§ 371 (c)(1),
(2) Date: Jul. 6, 2018

(87) PCT Pub. No.: WO2017/117666
PCT Pub. Date: Jul. 13, 2017

(65) Prior Publication Data
US 2019/0040451 A1 Feb. 7, 2019

Related U.S. Application Data

(60) Provisional application No. 62/276,630, filed on Jan. 8, 2016.

(51) Int. Cl.
*C12Q 1/68* (2018.01)
*C12Q 1/6806* (2018.01)
(Continued)

(52) U.S. Cl.
CPC ............ *C12Q 1/6806* (2013.01); *A61B 10/02* (2013.01); *B01L 3/5029* (2013.01);
(Continued)

(58) Field of Classification Search
CPC .. B01L 7/52; B01L 3/502715; B01L 2200/10; B01L 3/5029; B01L 2200/16;
(Continued)

(56) References Cited

U.S. PATENT DOCUMENTS 5,955,351 A * 9/1999 Gerdes ............... B01L 3/502
422/112
6,203,758 B1 * 3/2001 Marks ................. B01J 19/0046
204/403.01

(Continued)

FOREIGN PATENT DOCUMENTS

CA 2836608 A1 12/2012
WO 99/26724 A2 6/1999
(Continued)

OTHER PUBLICATIONS

Yeung et al "A DNA biochip for on-the-spot multiplexed pathogen identification" Nucleic Acids Researvh 2006, 34(18) e118, pp. 1-7. (Year: 2006).*

(Continued)

*Primary Examiner* — Betty J Forman
(74) *Attorney, Agent, or Firm* — Norton Rose Fulbright Canada

(57) ABSTRACT

A fully integrated and disposable point-of-care device for detecting a target nucleic acid is provided. The device comprises: an extraction chamber adapted to receive a biological sample, wherein said extraction chamber comprises means to extract and lyse the sample to release nucleic acid; a first amplification chamber in communication with the extraction chamber, wherein said amplification chamber
(Continued)

comprises means to trigger nucleic acid amplification of a target nucleic acid sequence to occur; and a detection chamber in communication with the amplification chamber, wherein said detection chamber comprises means to detectably label the target nucleic acid and means to detect a signal associated with labeled target nucleic acid, or a single chamber for amplification, detection and identification of multiple nucleic acid sequences.

24 Claims, 16 Drawing Sheets

Specification includes a Sequence Listing.

(51) Int. Cl.
| | | |
|---|---|---|
| C12M 1/02 | (2006.01) | |
| C12M 1/33 | (2006.01) | |
| C12M 1/34 | (2006.01) | |
| C12M 1/36 | (2006.01) | |
| C12M 1/30 | (2006.01) | |
| B01L 7/00 | (2006.01) | |
| C12M 3/06 | (2006.01) | |
| C12M 1/12 | (2006.01) | |
| A61B 10/02 | (2006.01) | |
| B01L 3/00 | (2006.01) | |
| C12Q 1/686 | (2018.01) | |
| C12Q 1/6844 | (2018.01) | |

(52) U.S. Cl.
CPC .......... *B01L 3/502715* (2013.01); *B01L 7/52* (2013.01); *B01L 7/525* (2013.01); *C12M 1/34* (2013.01); *C12M 1/36* (2013.01); *C12M 23/16* (2013.01); *C12M 25/16* (2013.01); *C12M 33/02* (2013.01); *C12M 41/22* (2013.01); *C12M 45/02* (2013.01); *C12Q 1/68* (2013.01); *C12Q 1/686* (2013.01); *B01L 2200/10* (2013.01); *B01L 2300/027* (2013.01); *B01L 2300/0663* (2013.01); *B01L 2300/1805* (2013.01); *C12Q 1/6844* (2013.01)

(58) Field of Classification Search
CPC . B01L 2300/0636; A61B 10/02; C12Q 1/686; C12Q 1/6806; C12Q 1/6844; C12Q 2537/101; C12Q 2565/629; C12Q 2547/101; C12Q 1/6825; C12Q 1/6848; C12N 15/1003; C12N 15/1006
See application file for complete search history.

(56) References Cited

U.S. PATENT DOCUMENTS

| | | | |
|---|---|---|---|
| 2006/0065531 A1 | 3/2006 | Smolko et al. | |
| 2009/0042280 A1* | 2/2009 | Yang ................... | B01L 3/5027 435/287.2 |
| 2009/0105082 A1 | 4/2009 | Chetverin et al. | |
| 2009/0186357 A1* | 7/2009 | Mauk ................... | B01L 3/5027 435/6.15 |
| 2009/0325276 A1* | 12/2009 | Battrell ............... | B01F 11/0071 435/287.2 |
| 2010/0056383 A1* | 3/2010 | Ririe ................... | B01L 3/50273 506/7 |
| 2010/0291666 A1* | 11/2010 | Collier ............... | C12N 15/1003 435/287.2 |
| 2011/0281754 A1 | 11/2011 | Fischer | |
| 2011/0308313 A1 | 12/2011 | Azimi et al. | |
| 2012/0329142 A1 | 12/2012 | Battrell | |
| 2014/0322706 A1 | 10/2014 | Kayyem | |

FOREIGN PATENT DOCUMENTS

| | | |
|---|---|---|
| WO | 2006071770 A2 | 7/2006 |
| WO | 2014022700 A3 | 2/2014 |
| WO | 2016004539 A1 | 1/2016 |

OTHER PUBLICATIONS

International Search Report and Written Opinion issued in International Application No. PCT/CA2017/000001, dated Mar. 28, 2017.
White et al, "High-Throughput Microfluidic Single-Cell Polymerase Chain Reaction", Analytical Chemistry, Jul. 2, 2013, vol. 85, pp. 7182-7190, ISSN 0003-2700.
Walker et al., "Collection of Genomic DNA by Buccal Swabs for Polymerase Chain Reaction-Based Biomarker Assays", Environmental Health Perspectives, Jul. 1999, vol. 107(7), pp. 517-520, ISSN L 0091-6765.
International Search Report and Written Opinion issued in International Application No. PCT/CA2015/050648, dated Oct. 9, 2015.
Taylor et al., "Dynamic Analysis of MAPK Signalling Using High-Throughput Microfluidic Single-Cell Imaging Platform", PNAS, Mar. 10, 2009, vol. 160(10), p. 3758-3763.
Supplemental European Search Report issued in European Application No. EP 15818542.1, dated Dec. 13, 2017.
Supplemental European Search Report issued in European Application No. EP 17735777, dated Sep. 13, 2019.
Gill, P. et al., "Detection of Helicobacter pylori by Enzyme-Linked Immunosorbent Assay of Thermophilic Helicase-Dependent Isothermal DNA Amplification", Diagnostic Microbiology and Infectious Disease, 2007, p. 243-249.
Hamidi, S. et al., "Real-Time Detection of H5N1 Influenza Virus Through Hyperbranched Rolling Circle Amplification", Analyst, 140, p. 1502-1509.
Kersting, S. et al., "Multiplex Isothermal Solid-Phase Recombinase Polymerase Amplification for the Specific and Fast DNA-Based Detection of Three Bacterial Pathogens", Microchim Acta, 2014, 181, p. 1715-1723.
Mahony, J. et al., "Multiplex Loop-Mediated Isothermal Amplification (M-LAMP) Assay for the Detection of Influenza A/H1, A/H3 and Influenza B Can Provide a Specimen-to-Result Diagnosis in 40 Min with Single Genome Copy Sensitivity", Journal of Clinical Virology, 2013, http://dx.doi.org/10.1016/j.jcv.2013.06.006.
Mahony, J. et al., Development of a Sensitive Loop-Mediated Isothermal Amplification Assay That Provides Specimen-to-Results Diagnosis of Respiratory Syncytial Virus Infection in 30 Minutes, Journal of Clinical Micorbiology, Aug. 2013, vol. 51, No. 8, p. 2696-2701.
McCalla, S. et al., "A Simple Method for Amplifying RNA Targets (SMART)", Journal of Molecular Diagnostics, Jul. 2012, vol. 14, No. 4, p. 328-335.
Roskos, K. et al., "Simple System for Isothermal DNA Amplification Coupled to Lateral Flow Detection", PLOS ONE, Jul. 2013, vol. 8, issue 7, p. 1-8.
Tan, E. et al., "Isothermal DNA Amplification with Gold Nanosphere-Based Visual Colorimetric Readout for Herpes Simplex Virus Detection", Clinical Chemistry, 2007, vol. 53, No. 11, p. 2017-2020.
Wang, D. et al., "Development of Primer Sets for Loop-Mediated Isothermal Amplification that Enables Rapid and Specific Detection of *Streptococcus dysgalactia, Streptococcus uberis* and *Streptococcus agalactia*", International Journal of Environmental Research and Public Health, 2015, 12, p. 5735-5742, doi:10.3390/ijerph120605735.
Wang, D. et al., "A Comparison of In-House Real-Time LAMP Assays with a Commercial Assay for the Detection of Pathogenic Bacteria", Molecules, 2015, 20, p. 9487-9495, doi:10.3390/molecules20069487.
First Office Action issued in corresponding Chinese Application No. 2017800145981, dated Jul. 2, 2021.

* cited by examiner

A)

B)

FULLY INTEGRATED HAND-HELD DEVICE TO DETECT SPECIFIC NUCLEIC ACID SEQUENCES

FIELD OF THE INVENTION

The present invention pertains to the field of point-of-need (PON) or point-of-care (POC) diagnostic devices, for example, for use in the detection of infectious diseases, and biomarkers for cancer and other chronic diseases.

BACKGROUND OF THE INVENTION

There has been a shift away from traditional testing methods for infectious diseases, such as culture and antigen detection, towards more sensitive nucleic acid amplification tests (herein referred to as NAAT). Polymerase chain reaction (PCR) amplification has provided laboratories with sensitive and specific tools to detect infectious diseases, and has been adopted by clinical laboratories around the world.

Current molecular diagnostic tools are limited by substantial "off-chip" clinical sample preparation time and the requirement for skilled technicians. This limits the application of molecular diagnostics in an at-home or resource-poor setting. Typical diagnostic tests may be completed within a time period ranging from 3 hours to 5 days. However, this does not provide useful diagnostic information in certain circumstances.

Using microfluidic devices to miniaturize diagnostic assays into a "lab on a chip" format has gained much attention in the last decade. Microfluidic devices are typically small and require very low sample volumes, which is conducive to molecular diagnostics. This technology may be useful to construct POC diagnostic tools for use, for example, at the bedside and to provide rapid diagnostic results. However, the cost of a POC device is important and should be as low as possible, especially for use in resource-poor settings. At this time, complicated and expensive sample preparation and DNA detection technologies have prevented the construction of an inexpensive, fully disposable POC device.

Devices have been developed which permit isolation of infectious particles (virus, bacteria or fungi) from a clinical sample (blood, urine, nasopharyngeal swab, fecal material) in an automated manner "on-chip", or without the need for human intervention. For example, WO110019A1 discloses a microfluidic platform that can bind pathogens or nucleic acid to magnetic beads, and subsequently move them to a secondary chamber for detection. In addition, WO122564A2 discloses a device for the release of intracellular contents from pathogens and subsequent transport of a portion of the contents for detection. US 2008/0299648A1 discloses a self-contained diagnostic kit that includes a sample collection element and an immunochromatography test strip. U.S. Pat. No. 8,574,923B2 discloses a sample preparation device that specifically binds nucleic acids using a monolith absorbent or using sample filters to bind any analytes of interest and lyse cell membranes. WO2012/013733A1 discloses a device for generic sample preparation to isolate nucleic acids from a variety of liquid matrices for diagnostic purposes. Finally, WO2013/158686A1 discloses a nucleic acid sample preparation device that requires minimal hands on time and can purify nucleic acids from various cellular mixtures.

In the detection of infectious disease, infectious particles are first isolated and then must be lysed to release intracellular contents, including DNA, RNA, and protein. While several methods have been characterized for releasing nucleic acids and proteins from cells, their integration into a diagnostic POC platform significantly increases the complexity of the device. For mechanical lysis, motor elements are required which can increase both the cost and complexity of the device. For chemical lysis, it is difficult to administer the correct amount of lysis reagent and subsequently remove the reagent before analysis downstream. NAAT techniques are particularly sensitive to chemical contamination and all lysis chemicals must be removed before next steps, including enzymatic amplification and detection.

Polymerase chain reaction (PCR) is a common technique used to amplify pathogenic DNA sequences to high concentrations using a combination of thermostable DNA polymerase and thermocycling. However, PCR typically requires thermocycling between ~50° C. and 95° C. for amplification to occur, and integration of thermocycling into a POC diagnostic platform would increase both the complexity and cost of developing a POC molecular diagnostic device.

The use of disposable systems for POC diagnostics is appealing for at-home testing, resource-poor settings or community hospitals without access to a central laboratory, but auxiliary systems required for read-out are typically expensive and dedicated, which limit their disposability. This can also result in an expensive initial capital investment for a stand-alone unit or reader.

Thus, it would be desirable to develop a portable and disposable diagnostic point-of-care device.

SUMMARY OF THE INVENTION

A stand-alone point-of-care device has now been developed which is adapted to receive a raw clinical sample (e.g. blood, urine, fecal material, nasopharyngeal swab and the like), release pathogen intracellular contents, amplify and detect specific nucleic acid sequences and display the results, without the intervention of any external equipment or devices. This fully-integrated stand-alone point-of-care device is also a single use, disposable device.

Accordingly, a fully integrated, stand-alone point-of-care device for detecting a target nucleic acid sequence is provided comprising:
an extraction chamber adapted to receive a biological sample for extracting and lysing the sample to release nucleic acid;
an amplification chamber for receiving amplification reagents for amplifying a target nucleic acid sequence;
a detection element in communication with the amplification chamber, the detection element comprising a detection agent that produces a detectable signal in association with the amplified target nucleic acid; and
a reading area for displaying the detectable signal.

In one embodiment, the extraction and amplification chambers are a single chamber and the detection element comprises a detection surface that may form a part of a wall of the amplification chamber. In one embodiment, the device includes amplification reagents for multiple target nucleic acid sequences, wherein distinct nucleic acid capture probes targeting the specific nucleic acid segments are coated onto specific locations of the detection surface enabling the detection of multiple target nucleic acids in a single chamber.

These and other aspects of the invention will become apparent by reference to the figures and description that follow.

DETAILED DESCRIPTION

Figure 1:
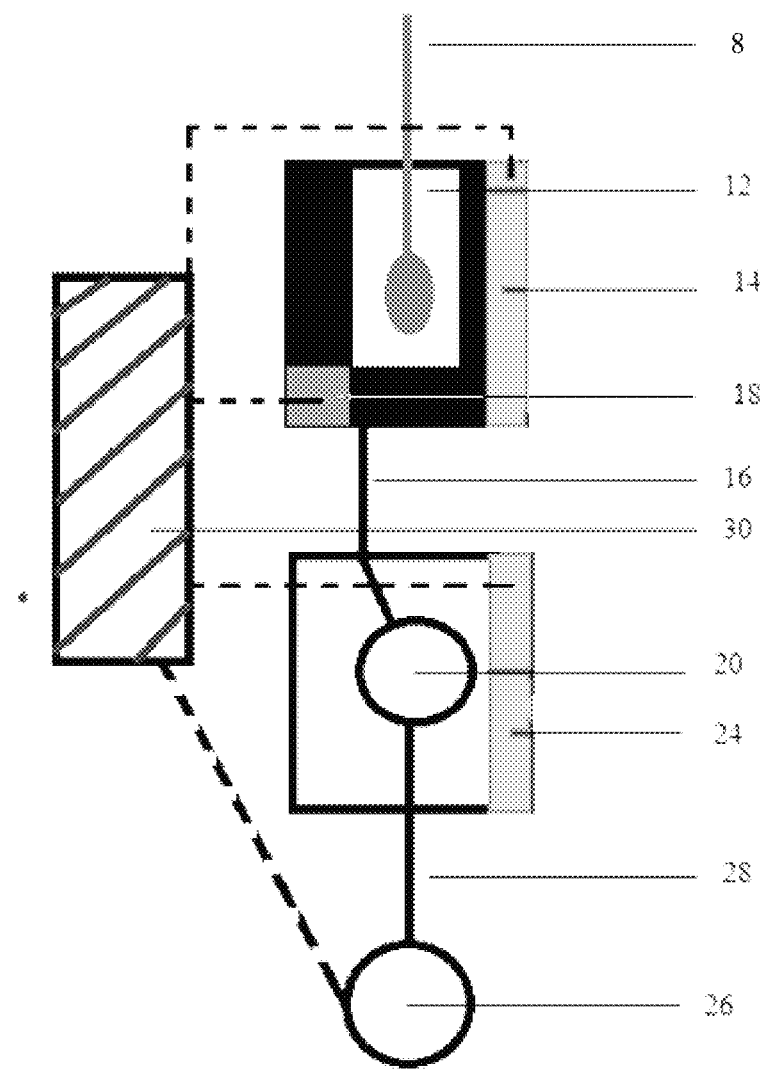
FIG. 1 is a block diagram of an embodiment of the invention (A); and a schematic of a POC device in accordance with an embodiment of the invention, with example dimensions where L is e.g. 2.75", W is e.g. 1.05", and D is e.g. 0.25" (B) including various views; and a photograph of the POC device in accordance with another embodiment of the invention (C).
Figure 1:
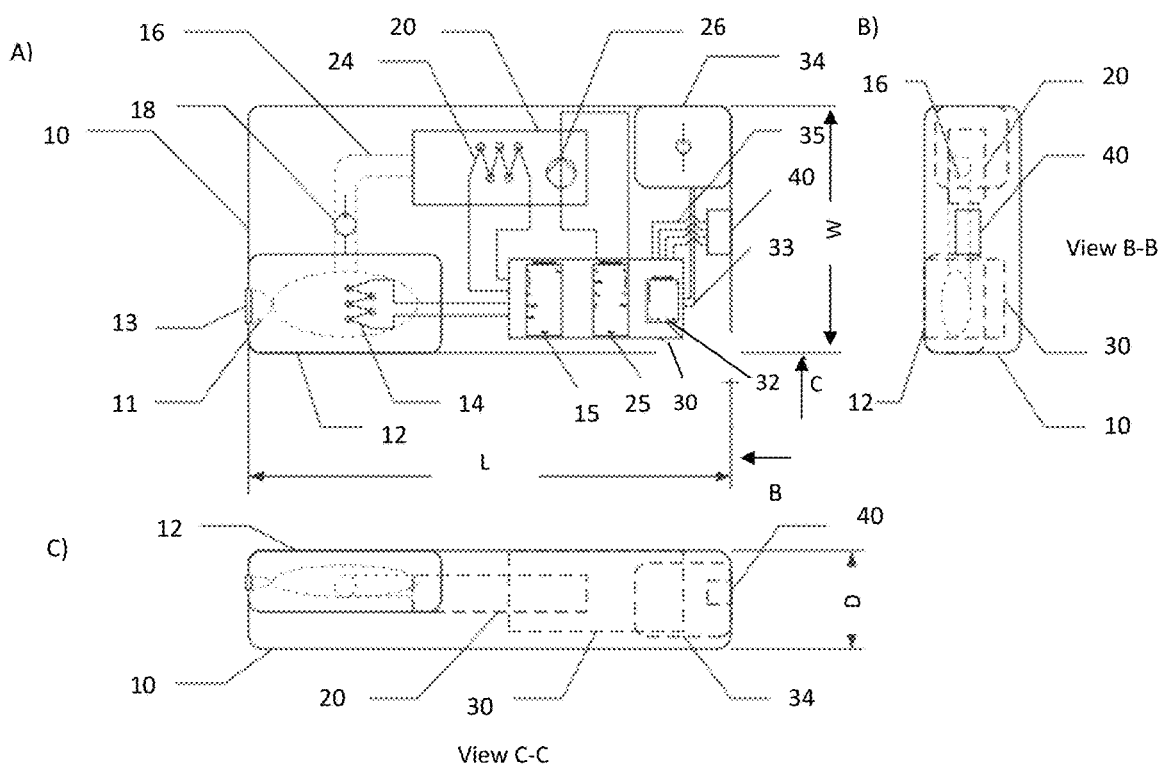
Figure 1:
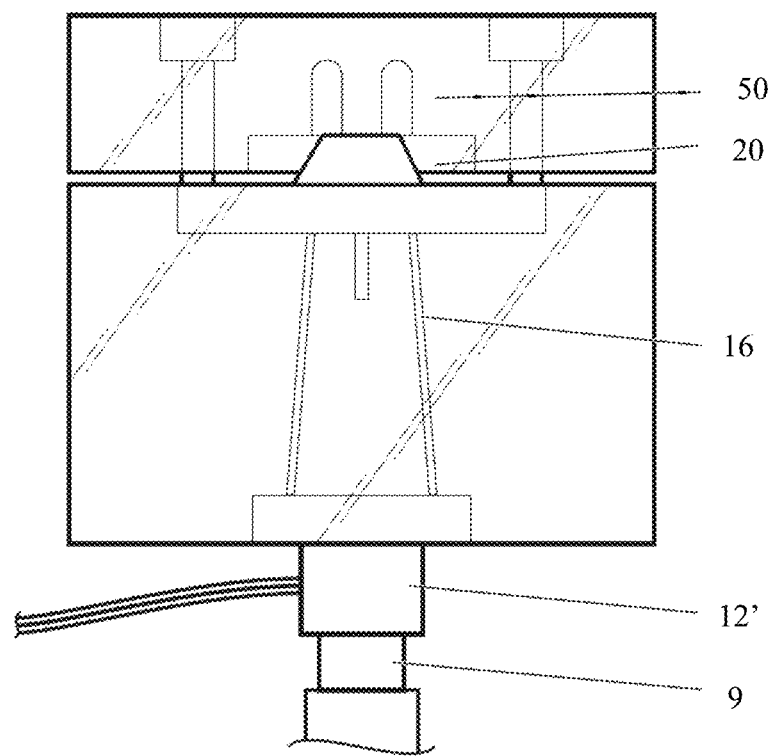

A fully integrated, stand-alone, single use point-of-care device for use in the detection of a target nucleic acid is provided (see, for example, FIG. 1A). The device comprises an extraction chamber 12 adapted to receive a biological sample and lyse the sample to release nucleic acid; a first amplification chamber 20 in communication with the extraction chamber 12 which receives an aliquot of the sample from the extraction chamber 12 and comprises a means to amplify a target nucleic acid in the sample; and a detection chamber, which in one embodiment is the same chamber as amplification chamber 20, while in another embodiment, is a separate detection chamber 50 in communication with the amplification chamber 12 comprising a means to label the target nucleic acid for detection and a means to detect the label. As used herein, the term "extraction chamber" refers to a chamber in which both sample extraction and lysis occurs.

In one aspect, the term "nucleic acid" is not particularly restricted and includes, but is not necessarily limited to deoxyribonucleic acid (DNA) and ribonucleic acid (RNA) (including e.g. specific mRNA transcripts or siRNA associated with disease), and nucleic acids may be from different sources e.g. bacterial, viral, animal (in particular human) and fungal. In one embodiment, the source is a pathogen.

The biological sample may be obtained using any appropriate vehicle for use to transfer the sample into the extraction chamber of the device. In one embodiment of the invention, a swab 8 is used to collect a nucleic acid-containing biological or clinical sample (e.g. blood, urine, nasopharyngeal swab, fecal sample, vaginal swab, tears, fluid excreted at wound sites or sites of inflammation, or any other clinical material that is nucleic acid-containing). As one of skill in the art will appreciate, the biological sample may be obtained by means other than a swab, e.g. by a syringe, or a collection vessel, into which the swab may be dipped. The sample-containing swab is placed in a swab-accepting opening in the extraction chamber of the device. The swab used may be a standard swab, or a swab designed specifically for the device. For example, the swab may be sized to fit within the extraction chamber to permit sealing of the opening of the chamber with a cap or lid. When a standard swab is used, the swab shaft may be broken at the opening of the chamber to permit sealing of the chamber opening with a lid. The swab may have a smaller head conducive for collecting certain samples such as vaginal and nasopharyngeal samples. Alternatively, the swab may include a plug along its shaft which functions to seal the opening of the extraction chamber and prevent leakage from the device. Once the extraction chamber is closed, it forms an enclosed contained environment within the device. Other appropriate vehicles for sample transfer include a stick, a foam-tipped shaft, or other vehicle capable of adsorbing the biological sample for transfer to the device.

The extraction chamber 12 comprises means to enable sample extraction, as required, and lysis to release nucleic acid from the sample. Thus, the extraction chamber 12 either contains or has access to a lysis solution suitable for extraction of sample from the delivery vehicle and lysis of the sample, for example, a phosphate buffered saline solution, water, a 0.1% Triton-X100 solution, a 0.1% SDS solution, other suitable detergents for extraction and lysis, or a combination of any of these. In one embodiment, the extraction chamber 12 includes an amount of the lysis solution suitable for extraction and lysis, e.g. a volume of about 0.2-0.5 mL of lysis solution, to immerse the sample-containing vehicle and facilitate sample extraction/lysis therefrom. In this case, the extraction chamber 12 is provided with a one-way point of entry (at or adjacent to the opening of the device), e.g. a membrane, which permits input of the sample into the extraction chamber 12 via a vehicle (e.g. swab or the like), but prevents leakage of lysis solution from the extraction chamber 12. In another embodiment, the extraction chamber 12 is in communication with a buffer-releasing means 152 which functions to release extraction and lysis solution into the extraction chamber 12 on entry of the sample into the extraction chamber 12. For example, the lysis solution may be contained in a pouch, blister pack or other reservoir, either within the extraction chamber 12 or adjacent to the extraction chamber 12, which is activated to release solution into the extraction chamber on entry of the sample. In this regard, the pouch or blister-pack may be pierced by the sample-containing vehicle (e.g. swab) on entry, pierced by means within the chamber on sealing of the chamber or closure of the lid, or burst by pressure within the chamber on sealing of the chamber. An adjacent reservoir may be caused to release lysis solution into the extraction chamber by similar piercing or bursting of a membrane connecting the reservoir to the extraction chamber. As will be appreciated by one of skill in the art, other means of releasing lysis solution from a pouch or reservoir may also be utilized.

On sealing of the extraction chamber, for example, by closure of the lid to the opening of the extraction chamber, the device is activated by completion of one or more circuits as will be described. Thus, heater(s), pump(s), and other electrical parts (as described) are appropriately powered by connection to a control unit, including a battery, either on-board or off-board (via connection to an external power source), via any appropriate adaptors (DC adaptor) and/or converters (D/A converter). The connection may be a standard electrical connection (DC adaptor) to a power source (e.g. battery), or the connection may be via a port (e.g. USB) to an external power source such as a processing device, e.g. computer, cell phone, tablet or other external device. Thus, the device may be provided with means to connect to a power source.

The extraction chamber comprises means to facilitate sample extraction and lysis to release nucleic acid therefrom. In one embodiment, a heating means, e.g. a self-regulating heater or laser/light/ultrasonic agitated metal surface heater that can be self-regulating by virtue of its design, is used to heat the extraction chamber to a temperature suitable to facilitate sample extraction and lysis, e.g. a temperature between about 88° C.-100° C. for a sufficient time period, e.g. at least about 2-3 minutes. Self-regulating heaters may include, but are not limited to, PTC (Positive Temperature Coefficient) ceramic heaters, evaporation temperature control heaters, or heat-sink temperature control heaters. The heater is activated when the lid of the extraction chamber is closed, thereby completing a circuit which connects the heater to a power supply, e.g. battery.

Alternatively, the extraction chamber may comprise means to generate a mechanical force, e.g. a small motor, to facilitate release of sample from the swab and lysis of any pathogen present. The motor may be combined with the use of glass or ceramic beads placed within the extraction chamber to accelerate lysis. The motor may be situated at the base of the extraction chamber, and is powered in the manner described for the heater. This embodiment may or may not additionally include a heater to facilitate lysis.

In certain samples, for example nasopharyngeal samples, pathogens can be lysed with heat and nucleic acid can be directly amplified without nucleic acid purification.

In other samples, for example blood or urine which contain nucleic acid amplification inhibitors (such as bile salts, heme, proteinases, urea, or hemoglobin), purification of nucleic acid within the extraction or amplification chamber may be required. In this case, the chamber may be coated with immobilized oligonucleotide capture probes that have a complimentary sequence to a target nucleic acid (e.g. in an amount of about $10^4$ to $10^5$ copies), (for example, such as those exemplified in Table 1). The device may optionally include a positively charged electrode within the extraction chamber which is powered or activated on closure of the lid of the device, to facilitate nucleic acid binding onto the capture probes. Once nucleic acid is bound to the probes, e.g. within a short period of time such as about 2 minutes, amplification inhibitors may be removed from the extraction or amplification chamber. Inhibitor removal may be accomplished by aspiration, or pumping, into a waste chamber or reservoir 154 connected to the extraction chamber, or contaminants may be washed into the waste chamber 154 with buffer released from a secondary buffer chamber. In addition to removing potential amplification inhibitors this step also concentrates the nucleic acid, e.g. DNA or RNA, prior to amplification. This nucleic acid capture step is performed between 95° C. and 63° C., as the lysis mixture is cooling without the need for a heater. Following target capture, the means used to remove contaminants from the extraction chamber 12, e.g. micro-pump and/or buffer-releasing means, is activated as previously described, and may utilize a timer so that waste removal occurs following capture of all or a sufficient quantity of nucleic acid. Nucleic acid may then subsequently be eluted as previously described.

As used herein, capturing beads refer to microbeads having capture probes immobilized thereon, or having electric charge or binding structures that allow for the capture of nucleic acid (e.g. DNA). These capture beads may be preloaded into the lysing chamber, amplification chamber and/or detection chamber. Capturing beads may be designed to capture any nucleic acid (e.g. DNA), such as by having an electric charge. Capturing beads may also be designed to capture a specific DNA segment by using microbeads having thereon a capture probe specific to a target nucleic acid (e.g. DNA), to capture, for example an amplified nucleic acid (e.g. DNA) segment. In embodiments where multiple amplified nucleic acid (e.g. DNA) segments are present, capturing beads having microbeads with different properties may be used to detect different amplified nucleic acid (e.g. DNA). Each subset of microbeads having a particular property may have immobilized thereon a capture probe for a particular amplified nucleic acid (e.g. DNA) segment. These different properties (e.g. size, magnetic versus non-magnetic) enable the microbeads to be separated based on these properties, and in turn allow for the detection of different amplified nucleic acid (e.g. DNA).

In one embodiment, biotin-labeled nucleic capture probes are immobilized onto commercially available streptavidin-coated microbeads (Invitrogen) which micro beads are preloaded as described above.

In some embodiments, capturing bead can be separated based on size. The size of the microbeads suitably range from 1-200 microns in diameter, and may for example be made of a polymer material. Microbeads are commercially available in various sizes and properties. Example micro beads include but are not limited to Thermo Fisher Scientific Dynabeads. The captured nucleic acid (e.g. DNA) are collected by collecting settled capturing beads bound with DNA. In some embodiments, the capturing beads settle in different layers based on the different sizes of the microbeads, allowing for the detection of different amplified nucleic acid (e.g. DNA) segment and indications. Preferably, capturing beads with different sizes are selectively collected using correspondingly sized filters. In one embodiment, at most three different microbead sizes are used. In another embodiment, two different microbead sizes are used.

In some embodiments, magnetic beads are used which allow for magnetic separation and collection of the magnetic beads from non-magnetic beads by applying a magnetic field. These magnetic and non-magnetic beads may further have different sizes to allow for the detection of further indications. The capturing beads may also be distinguished and separated based on other features.

Alternatively in other embodiments, nucleic acid capture probes are coated onto and immobilized onto the wall of the lysing chamber, amplification chamber and/or detection chamber using, for example, carbodiimide crosslinking methods for nucleic acids (Thermo Fisher Scientific). By localizing different capture probes to different locations of the chamber, this approach allows for the detection of a greater number of indications or different amplified DNA segments than using capturing beads. In other embodiments, the capturing beads, including magnetic beads, may be immobilized onto the wall of the chamber using immobilizing methods known to the person skilled in the art. Such immobilizing methods include, for example, covalent bonding methods. In yet other embodiments, both nucleic acid capturing beads and wall coating are used. For example, the capturing beads may capture any nucleic acid to allow for amplification while the wall coating are designed to capture specific nucleic acid to allow for detection, or vice versa. Or in another example, both capturing beads and/or the wall coating may be designed to capture specific amplified nucleic acid. Other combinations are also possible.

Figure 9A:
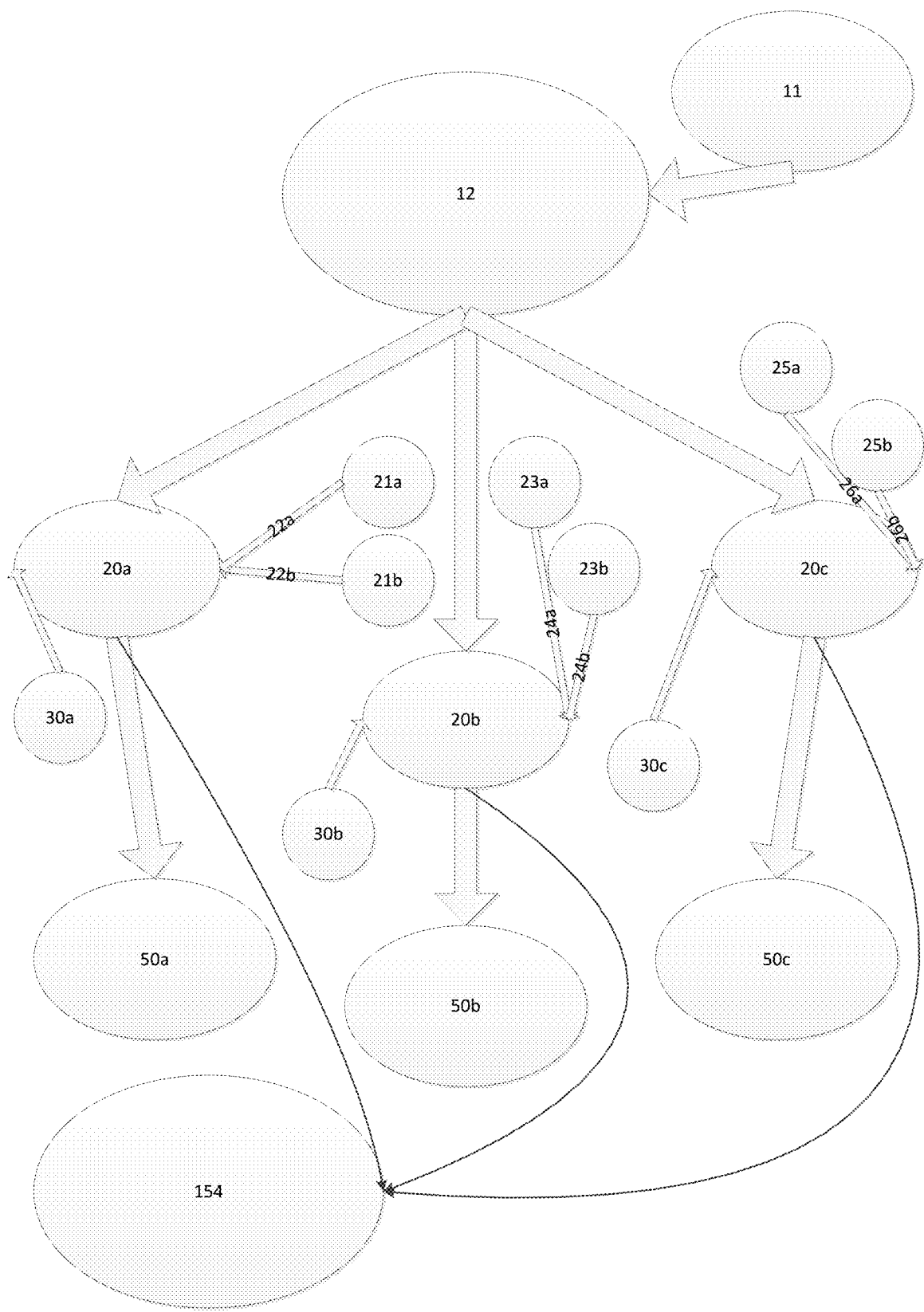
FIG. 9a is a block diagram of a device with a single lysis chamber and multiple channels for amplification and detection of specific nucleic acid sequences including multiple wash steps.

FIG. 9a shows schematically an exemplary embodiment with a single lysis chamber 12 and multiple amplification chambers 20a, 20b and 20c, each containing a single immobilized capture probe with dual washing steps prior to amplification. Suitably, in use, amplification chambers are kept at >90° C. to maintain the DNA in single-strained status, then allowed to cool down to about 63° C. for DNA to bind with preloaded DNA capturing beads and/or wall coating. In the case of e.g. a blood sample, the chambers are then suitably washed twice using wash fluid (21a, 21b, 23a, 23b, 25a, 25b) to remove the inhibitors from the blood. Then, the primer fluids (30a, 30b, 30c) are introduced into the amplification chambers 20a, 20b, 20c. The chambers are then heated up to the temperature range of 63° C.+/−5, more preferably in a target range of 63° C.+/−2, for a minimum 18 minutes amplification. In one embodiment, extraction chamber 12 suitably has a volume in the range of 250 µl+/−20% with a target volume in the range of 100 µl+/−20%. In one embodiment, amplification chambers have a volume of in the range of 25 µl+/−20% and are preloaded with DNA capturing beads or a DNA capturing wall coating. For example, amplification chamber 20a may be loaded with a primer 30a for detection of a first indication, amplification chamber 20b may be loaded with a primer 30b for detection of a second indication and amplification chamber 20c may be loaded e.g. with a quality control primer 30c that enables a user to confirm proper functioning of the diagnostic device. While the exemplary device shown in FIG. 9a has three amplification chambers 20a, 20b and 20c, the device may have more or less amplification chambers and, while not particularly restricted, suitably the device has between 1 and 50 number of amplification chambers. Amplification chambers 20a, 20b and 20c are shown connected to detection chambers 50a, 50b and 50c, although as previously provided, in an alternate embodiment, detection may be performed in amplification chambers 20a, 20b and 20c. While the exemplary device shown in FIG. 9a has three detection chambers 50a, 50b and 50c, the device may have more or less detection chambers and, while not particularly restricted, suitably the device has between 1 and 50 number of detection chambers. More preferably, the device has between 10 and 20 chambers to allow sufficient detection of different indications when performing multi-pathogen analysis. For example, a standard flu diagnosis may often involve the detection of 7 to 8 different pathogens. While a high-number chamber complicates the structures of the microfluidic channels, which in turn adds to production costs and reduced portability of the device. In one embodiment, detection chambers suitably have a volume range of 50 µl+/−20% and are preloaded with 25 µl+/−20% of dye for nucleic acid detection. As provided above, in use, once nucleic acid is bound to the probes, amplification inhibitors may be removed e.g. by washing, aspiration or pumping, into waste chamber 154. In one embodiment, waste chamber 154 has a reservoir volume in the range of 150 µl~3 ml.

Figure 9B:
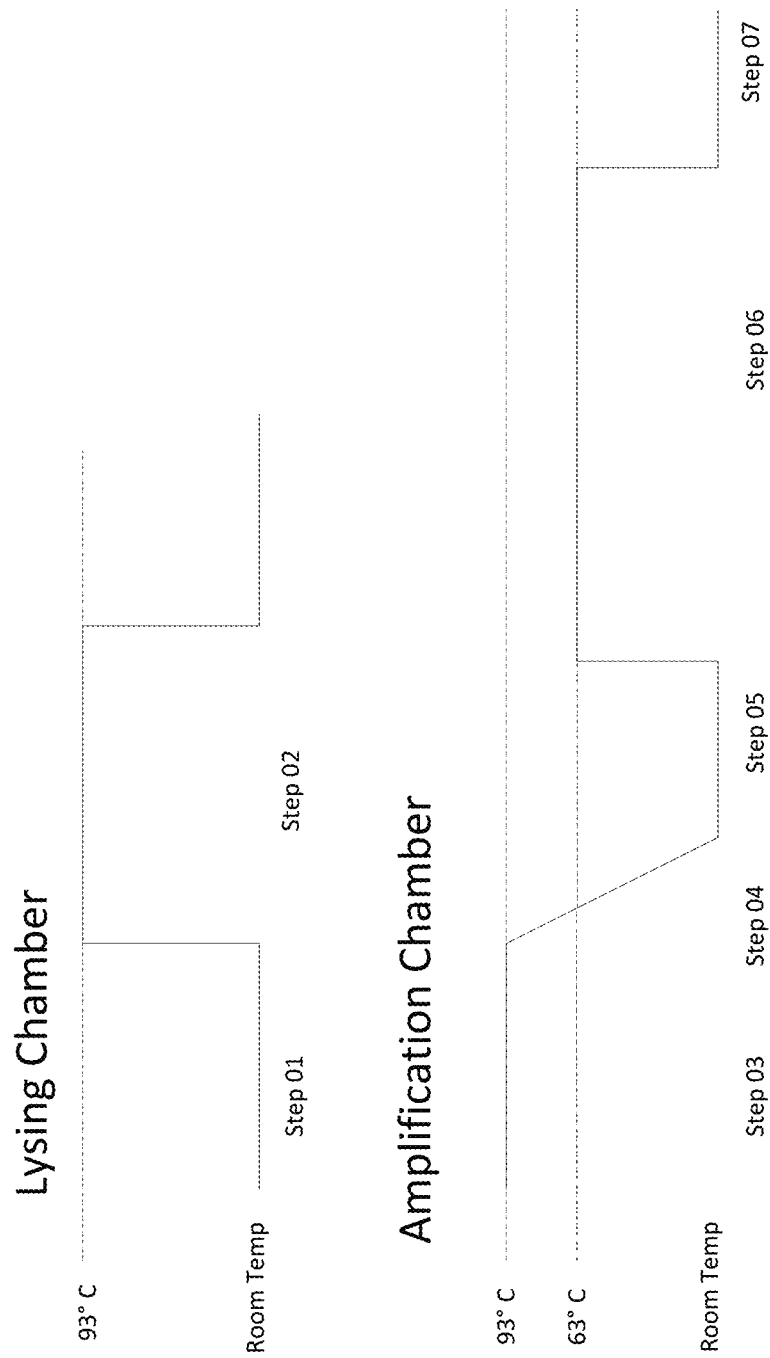
FIG. 9b shows the temperature profiles in the lysis and amplification chambers of a single or multiple channel device including washing steps.

FIG. 9b shows exemplary temperature profiles in the extraction chambers(s) and amplification chamber(s) with a dual wash implementation such as shown in FIG. 9a. The temperatures within the chambers vary while going through the following steps: Step 01—Swab Elution; Step 02—Lysing; Step 03—Post lysing, fluid enters amplification chamber at 90° C. to maintain single strand DNA phase; Step 04—Amplification chamber cools to allow binding of the DNA to beads or walls of chamber (DNA cannot leave the chamber during wash); Step 05—X2 Wash bound DNA; Step 06—Primer enters amplification chamber and is heated to 63° C. (DNA is unbound by amplification process); Step 07—At end of amplification, fluid moved to detection chamber.

Following lysis and nucleic acid release, a measured volume (e.g. about 5-10 µl) of this lysed material is transferred, for example by a micro-pump, to the amplification chamber via a channel, such as a microfluidic channel. The micro-pump may be powered by an on-board power source, such as a battery, or through connection to an external power source, as described. The pump is activated at the appropriate time, e.g. once sample extraction and lysis is complete, to transfer lysed material to the amplification chamber. In one embodiment, activation of the pump is delayed by a timer, connected to the power supply, to ensure that the sample undergoes extraction and lysis, and thereby to prevent transfer of unlysed material to the amplification chamber. Regarding transfer of a measured volume of lysed material, this may be controlled by a microcontroller. Alternatively, the volume of lysed material transferred into the amplification chamber may be controlled by the size of the amplification chamber (e.g. sized to contain a sufficient amount of amplification mixture and the desired amount of lysed material). In this case, the entrance to the amplification chamber may be covered by a hydrophobic membrane that permits output of gases from within the amplification chamber as it is filled, and input of liquid into the chamber until the chamber is filled.

The amplification chamber contains an amplification mixture which enables nucleic acid amplification to occur. The amplification mixture present in the amplification chamber may be lyophilized (optionally stabilized with pullanan or trehalose), in which case about 25 to 50 µl of lysed solution is added to the well. The amplification may also be in liquid form, in which case about 5 to 10 µl of lysed solution is added to the well. The amplification mixture contains oligonucleotide primers for amplification of target nucleic acid sequences (e.g. about 0.2 to 1.8 µM), a strand-displacement DNA polymerase, such as *Geobacillus stearothermophilus* polymerase or Taq polymerase (e.g. about 8 units), deoxynucleoside triphosphates or dNTPs (e.g. about 15 to 30 mM of each), buffer (e.g. about 1× final concentration), cation such as magnesium (e.g. about 2.0 to 8.0 mM). When the target nucleic acid is RNA, the amplification mixture additionally includes a reverse transcriptase. As one of skill in the art will appreciate, the oligonucleotide primers are selected to amplify a particular target DNA sequence from a target microorganism. Thus, to amplify a target sequence, primers (e.g. comprising from about 10 up to about 100 bases) which are complementary to a DNA sequence within the target microorganism are utilized. As one of skill in the art will appreciate, the number of oligonucleotide primers in the amplification mixture will vary with the amplification technique used, and primers in both the 5'-3' orientation as well as 3'-5' orientation may be used. In one embodiment, the target microorganism is a pathogenic organism such as, but not limited to, *Escherichia coli, Listeria monocytogenes, Clostridium difficile, Mycoplasma pneumonia, Chlamydia pneumoniae, Chlamydia trachomatis, Legionella pneumophilia, Neisseria gonorrhea, Streptococcus* sp. including Group A or Group B streptococcal infection, Herpes, papillomavirus, *Staphylococcus* sp. including Methicillin-resistant *Staphylococcus aureus* (MRSA), Influenza virus, Respiratory Syncytial Virus, Norovirus, West Nile Virus, Dengue Virus, SARS Co-V, Ebola virus, Lassa fever virus, Tuberculosis, HIV, Middle East respiratory syndrome coronavirus, and Chikungunya virus. Examples of primers used to amplify some of these pathogens can be found in Table 1.

In one embodiment, amplification is accomplished by an isothermal amplification technique, including but not limited to, nucleic acid sequence-based amplification (NASBA), transcription-mediated amplification (TMA), loop-mediated isothermal amplification (LAMP), cross-priming amplification (CPA), recombinase polymerase amplification (RPA), rolling circle amplification (RCA), helicase-dependent amplification (HDA), single-mediated amplification of RNA technology (SMART), nicking enzyme-mediated amplification (NEMA), isothermal chain amplification (ICA), Smart amplification (Smart-AMP), exponential amplification reaction (EXPAR), or ramification amplification (RAM). During amplification, the chamber is heated to a temperature suitable for amplification, e.g. a temperature between about 58° C. to 66° C., for a sufficient period of time, e.g. about 15-20 minutes, using a heater, such as a self-regulating heater or laser/light/ultrasonic agitated metal surface heater that can be self-regulating by virtue of its design. The heater is activated at the appropriate time, e.g. on or slightly prior to transfer of lysed material into the amplification chamber. In one embodiment, activation of the heater is delayed by a timer, connected to the power supply, to prevent premature heating within the amplification chamber.

In another embodiment, amplification may be accomplished by pH cycling-dependent amplification. In this case, the pH of the solution is cycled, for example from about pH 3 to about pH 8, to denature and renature the nucleic acid, thereby allowing polymerase access and subsequent amplification. For example, the amplification chamber may comprise a hydrogen-loaded plate dividing the amplification chamber into two sections. Electric field generated by two electrodes on either side of the plate pull hydrogen ions back and forth, cycling the pH. This is controlled by an electrical or mechanical timer to activate the electrodes on either side of the plate.

Electrical-Field amplification (EFA) may also be used for nucleic acid amplification whereby an electric field is applied to denature the DNA and thereby to allow access by the polymerase without the need for thermocycling. In this case, an electric field in the range of about 0.01 to 0.1 mV is generated by applying a voltage across electrodes located at opposite sides of the amplification chamber using a suitable power source. The voltage is activated and deactivated (to cause denaturing followed by renaturing and amplification) at specific intervals of between 10 and 20 seconds using a mechanical or electrical timer.

In another embodiment, the device is adapted for use to perform thermal cycling PCR amplification in the amplification chamber. For this approach, the self-regulated heater within the amplification chamber is activated and deactivated at specific time intervals (e.g. 20-40 s) using a mechanical or electric timer to cause heating up to a denaturing temperature, e.g. 94-96° C., and cooling to an annealing/amplification temperature, e.g. about 70° C. Temperatures are monitored with a thermistor connected to the microprocessor. As one of skill in the art will appreciate, the temperatures utilized and their time intervals may vary with the polymerase used, the concentration of divalent ions and dNTPs in the reaction, and the melting temperature of the primers.

The device may optionally include a second (parallel) amplification chamber to amplify nucleic acid sequences within the sample to serve as an amplification control. Thus, the second amplification chamber will include amplification mixture, along with oligonucleotide primers directed to the control nucleic acid sequence, such that when the device is activated, amplification of the control sequence occurs. While any suitable control sequence may be used, as one of skill in the art will appreciate, examples of control sequences include human genes such as human β-actin, as well as nucleic acid sequence from commensal bacteria such as *Streptococcus pyogenes* or *Staphylococcus epidermidis*. Thus, amplification of the control sequence will confirm that the sample was properly obtained, extracted and lysed, and that amplification properly occurred within the device, and that lack of a signal for the target microorganism is due to lack of target sequence within the sample as opposed to malfunction of the device.

Following amplification, the presence of target nucleic acid may be detected using a variety of methods including but not limited to: electrochemical detection, lateral flow-based detection, fluorescence detection, or colorimetric detection. This step is completed either within the amplification chamber or in a separate detection chamber, whereby a portion of the fluid is transported to a detection chamber using a micropump powered as previously described and using a timer to delay transport of fluid into the detection chamber until amplification is complete. Detection of DNA amplification may be performed directly in the amplification chamber in the presence of a detection sensor such as electrochemical detectors (e.g. potentiostat), light detectors (e.g. photodiode, fluorometer), colorimetric detector (e.g. light meter), and the like. Alternatively, detection may be performed in a separate detection chamber including a detection sensor. For colorimetric detection, the detection sensor may be a window that permits viewing of a colour change within the detection chamber.

Figure 5:
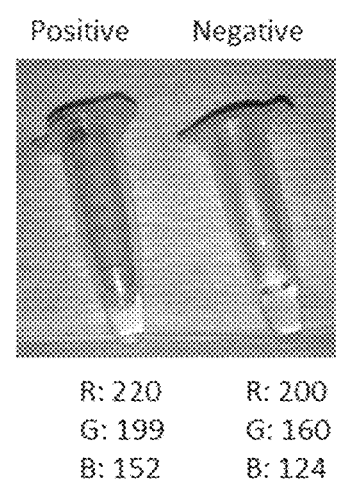
FIG. 5 illustrates analysis of a visual colour change and red, green, blue spectral analysis before and after amplification using Quant-iT PicoGreen DNA binding dye.

To enable detection of amplified nucleic acid, it is labeled with a DNA-binding detectable label, including but not limited to fluorescent, chemiluminescent, chromogenic labels, and electrochemically detectable labels. Examples of suitable DNA-binding detectable labels include methylene blue dye, leucocrystal violet, Quant-iT PicoGreen, fluorescent dye Calcein, or cyanine DNA binding dyes. FIG. 5 shows the red, green, blue spectral analysis of the Quant-iT Pico Green dye color change following amplification of a positive and negative sample. Colorimetric detection electronics integrated in the POC device will pick up different RGB readings of the positive and negative samples, and then give the display of samples being positive or negative.

In one embodiment, a DNA-binding detectable label is present in the amplification mix and binds to DNA as the DNA concentration increases by intercalating into the double helix of DNA. The amount of DNA-binding detectable label added to the amplification chamber is an amount in the range of about 5 to 10 µl. The labeled DNA, e.g. DNA/methylene blue complex, migrates differently to unbound label, e.g. methylene blue alone, in the presence of an electric field, which is used as a measure of DNA concentration. The electric field is provided by electrodes present within the amplification chamber and submerged in the sample. The electrodes are connected to a potentiostat which provides the voltage, after which peak anodic current is measured and relayed to an on-board or external microprocessor.

DNA amplification may be monitored using a DNA binding fluorescent dye. Examples of suitable DNA-binding fluorescent dyes include but are not limited to SYBR green, SYTO 9, SYTO 80, hydroxynapthol blue, or Quant-iT PicoGreen, either in the amplification chamber or a separate detection chamber. The amount of DNA-binding fluorescent dye used for detection is an amount in the range of about 5 to 10 µl. The device may be equipped with a fluorescent detector connected to the amplification or detection chamber, and a processing unit to provide a processed output. Alternatively, the signal from the detector may be transferred to an external processing unit to provide a processed output.

Amplification of DNA may be detected colorimetrically using gold nano-particles, DNAzymes, pH indicator dyes, or DNA binding dyes as described above, that trigger a colour change in the presence of DNA. This colour change may be detected manually (by eye) through a window which permits viewing into the detection chamber, using an on-board colorimetric detector connected to the detection or amplification chamber, or using an off-board detection means to which the detection chamber is connected as described, e.g. to analyze a color image of the solution following reaction with a colorimetric label by analysis of the colour change, such as RGB analysis. This may also be accomplished by shining a matching colour light onto the final amplified reaction mixture and monitoring the colour intensity as an output with a light meter.

Amplified DNA may be detected using lateral flow assay in the amplification chamber or a detection chamber. Multiple arrangements for detection using lateral flow assay are possible. In one embodiment, the amplified DNA is tagged with a ligand (e.g. biotin or another ligand) and labeled-oligonucleotide primers to the target nucleic acid (e.g. labeled with a fluoroscein label such as 6-carboxyfluorescein or fluorescein isothiocyanate (FITC), or another label), subsequently complexed using a binder to the ligand (e.g. avidin or streptavidin) and captured by immobilized antibody (e.g. anti-FITC antibody). As described above, the captured amplified DNA is then detected based on the label used, e.g. by a fluorescent or colorimetric signal, as described above.

In another embodiment of the device, detection is performed in a separate detection chamber containing a DNA binding dye which cannot be present during amplification, e.g. Hoechst dye. The amount of DNA-binding dye used for detection is an amount in the range of about 5 to 10 µl. DNA binding is monitored by electrochemical detection in the presence of an electric field as described for methylene blue DNA binding.

The detection chamber may optionally be a vial removably connected to the outside of the device that is amenable to subsequent analysis.

In one embodiment, the device may be adapted such that lysis and amplification occur in a single chamber, while detection occurs in a separate detection chamber. In this case, the lysis-amplification chamber suitably includes a self-regulated heater which is activated and deactivated at specific time intervals using a mechanical or electric timer to allow for heating up to a denaturing temperature, e.g. 95° C. and cooling to an amplification temperature, e.g. about 70° C. Amplified DNA may then be transported, for example via a pump, into a separate detection chamber for detection as previously described.

In another embodiment, the device may be adapted to detect two or more pathogens or gene targets. In this embodiment, the device may comprise two or more amplification chambers, each adapted to amplify the nucleic acid of a different target organism. Thus, each of the amplification chambers of this embodiment of the device will include an amplification mixture targeted to a different microorganism or gene target, including oligonucleotide primers. For example, the first amplification chamber may include oligonucleotide primers for *Escherichia coli*, while the second amplification chamber includes oligonucleotide primers for *Listeria monocytogenes*, and the third amplification chamber includes oligonucleotide primers for *S. pyogenes*. In another example, the device may include amplification chambers targeted to various skin infections, such as Herpes, papillomavirus and *C. trachomatis*. The device may be adapted for use in a third world country, and include amplification chambers each adapted to identify relevant target organisms such as, but not limited to, Dengue Virus, SARS Co-V, Ebola virus, Lassa fever virus, Tuberculosis and/or HIV or antibiotic resistance genes such as betalactamase, extended spectrum betalactamase (ESBL) or carbapenemases.

Figure 10:
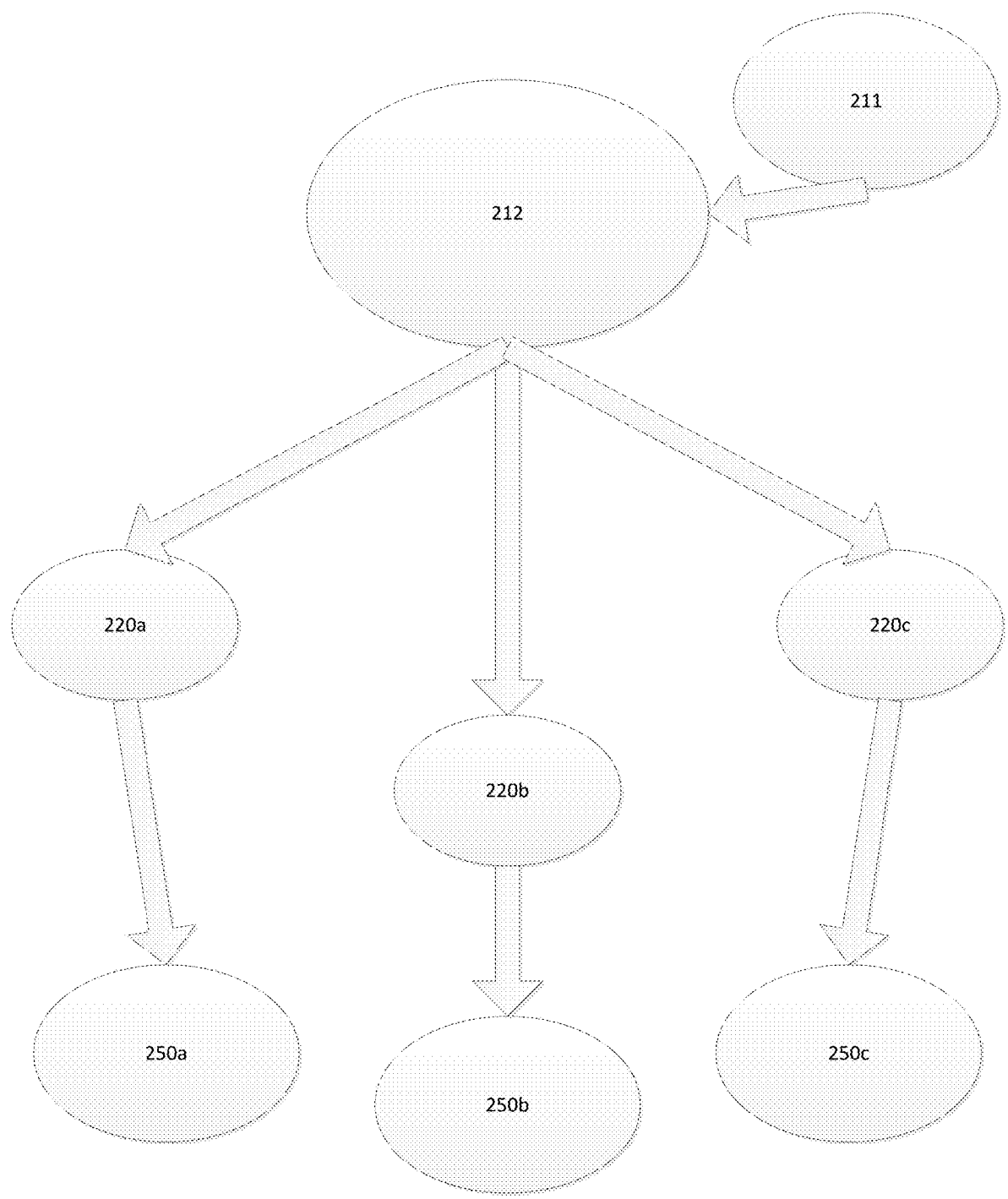
FIG. 10 is a block diagram of a device with a single lysis chamber and multiple parallel channels for amplification and detection of multiple specific types of nucleic acid with the wash steps not included.

FIG. 10 shows schematically an exemplary embodiment with a single lysis chamber 212 and multiple amplification chambers 220a, 220b and 220c, each preloaded with specific primers for the amplification of specific DNA segments. This simplified implementation does not require multiple washes to remove amplification inhibitors, which is most suitable for use with samples that lack amplification inhibitors or amplification processes that are more tolerant against amplification inhibitors. For example, a blood sample often contains proteins and/or microorganisms that bind to enzymes and primer used in amplification, thereby inhibiting the amplification of desired DNA segments. On the other hand, a throat swab, for example, tends to have less amplification inhibitors. The samples are first extracted and lysed at >93° C. for minimum 2.5 minutes to extract DNAs. Once the lysed biological samples are moved into amplification chambers, the chambers are then heated up to 63° C.+/−5, more preferably in a target range of 63° C.+/−2 for a minimum 18 minutes amplification. In one embodiment, extraction chamber 12 suitably has a volume range of 250 µl+/−20% with a target volume in the range of 100 µl+/−20%. In one embodiment, amplification chambers have a volume in the range of 25 µl+/−20% and are preloaded with specific primers. For example, amplification chamber 220a may be loaded with a primer for detection of a first indication, amplification chamber 220b may be loaded with a primer for detection of a second indication and amplification chamber 220c may be loaded e.g. with a quality control primer that enables a user to confirm proper functioning of the diagnostic device. While the exemplary device shown in FIG. 10 has three amplification chambers 220a, 220b and

220c, the device may have more or less amplification chambers and, while not particularly restricted, suitably the device has between 1 and 50 number of amplification chambers. Amplification chambers 220a, 220b and 220c are shown connected to detection chambers 250a, 250b and 250c, although as previously provided, in an alternate embodiment, detection may be performed in amplification chambers 220a, 220b and 220c. While the exemplary device shown in FIG. 10 has three detection chambers 250a, 250b and 250c, the device may have more or less detection chambers and, while not particularly restricted, suitably the device has between 1 and 50 number of detection chambers. More preferably, the device has between 10 and 20 chambers. In one embodiment, detection chambers suitably have a volume in the range of 50 µl+/−20% and are preloaded with 25 µl+/−20% of dye for nucleic acid detection.

In another embodiment, the device may be adapted such that lysis, amplification and detection is performed in a single chamber. To accomplish this, the swab or other vehicle containing the clinical sample is immersed into a single chamber containing amplification mixture (e.g. heat-stable DNA polymerase and/or reverse transcriptase for RNA targets, magnesium, nucleotides, nucleic acid primers for a specific target, and a DNA binding dye). The chamber including a self-regulating heater is activated by a timer to heat to a temperature of about 95° C. to lyse pathogens. Alternatively, free DNA/RNA is amplified without the need for heating to 95° C. In this case, the heating step can be omitted. The heater is then deactivated to permit cooling of the entire sample to a temperature between about 50-70° C. for DNA amplification. Following DNA amplification, the DNA binding dye will react with any amplified DNA and result in a colour change within the single chamber which may be detected as previously described.

Figure 11:
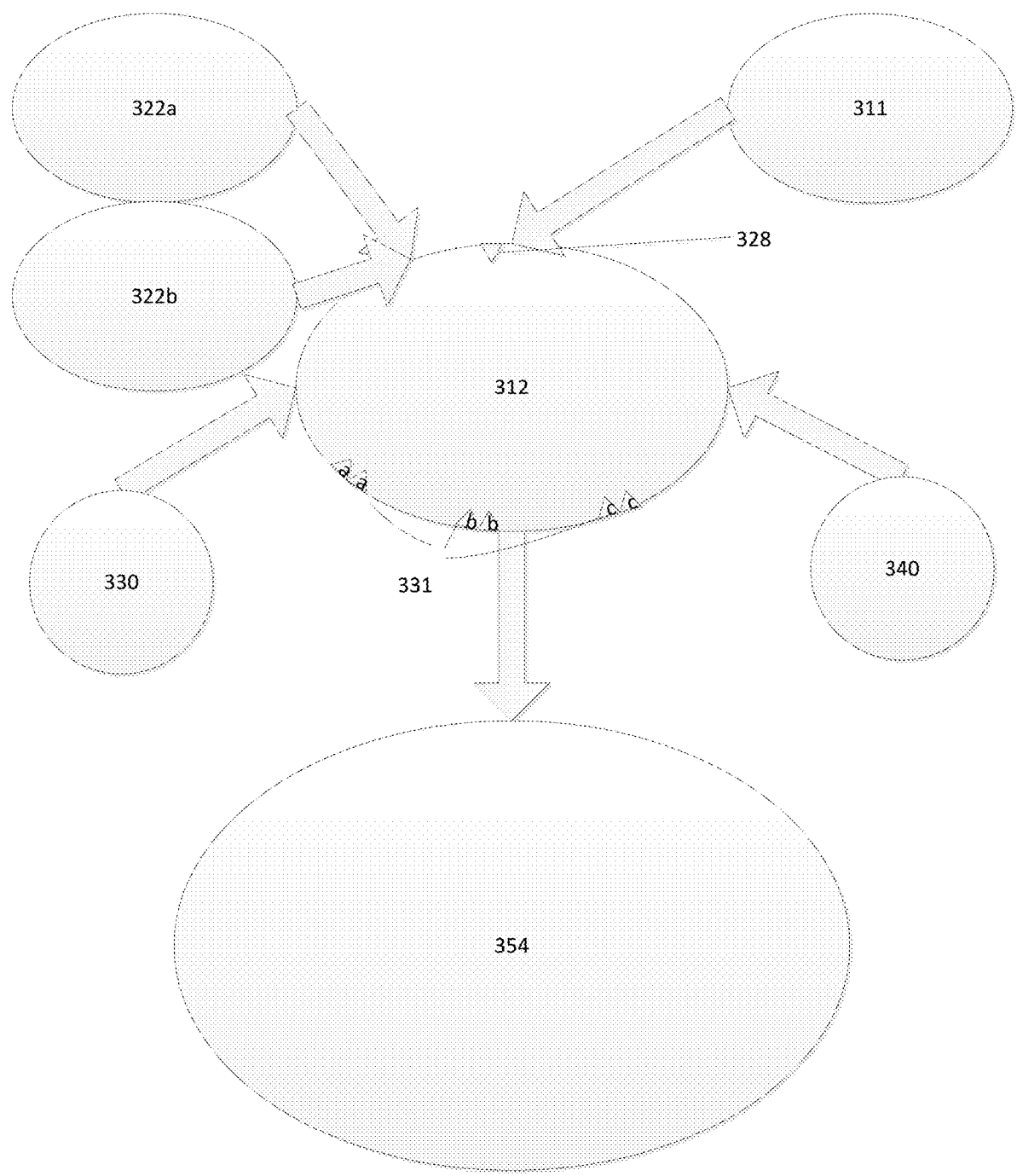
FIG. 11 graphically illustrates a design of a single chamber device for lysis, amplification, and detection of multiple pathogens employing specific locations for nucleic acid capture.

A single chamber design for lysis containing multiple nucleic acid capture sites to initiate amplification and multiple nucleic acid capture sites to capture amplified product for detection is shown schematically in FIG. 11. Lysing, amplification and detection chamber 312 suitably has a volume of 1 ml with a target loading of 500 µl. Once the sample swab is inserted, buffer fluid 311 (with chemical lysing agent) is loaded into the chamber to extract the DNAs. Alternatively, the buffer fluid does not contain lysing agent and the chamber is suitably heated to 93° C. or above to enable lysing. The chamber is preloaded with nucleic acid capturing beads and/or wall coating for capturing DNA (shown schematically as 328 on the wall of the chamber). Prior to the amplification, wash fluid 322a and 322b flush the chamber to remove any inhibitors. Nucleic acid segment capturing wall coatings for capturing amplified DNA segments (shown schematically as 331a, 331b and 331c on the wall of the chamber) are provided at different locations for different indications and/or detection of multiple pathogens. Dye mix 340 is then introduced to bind with captured DNA segments for detection. In this embodiment, a suitable volume for the waste reservoir may be e.g. 3 ml or greater. The lysing, amplification and detection chamber 312 is suitably connected to one more reservoirs of wash fluid, buffer fluid, primer mix 330 and dye mix. In this embodiment, the nucleic acid capturing beads and/or wall coatings 328, 331a, 331b, and 331c are shown located within a spherical single chamber 312, which are simultaneously immersed when fluid fills the chamber. Alternatively, the single chamber 312 can have an elongated shape, in which the nucleic acid capturing beads and/or wall coatings 328, 331a, 331b, and 331c are located along the longitudinal axis of the chamber, and in preferred embodiments the capturing beads and/or wall coatings are arranged in series. This allows a sequential fluidic immersion of nucleic acid capturing beads and/or wall coating 328, 331a, 331b, and 331c. In yet other embodiments, the single chamber 312 may comprise other shapes. In all cases, the capturing beads are sized to allow passage of the fluid through the chamber.

In an embodiment, in which sample extraction, lysing, amplification and detection are accomplished in a single chamber, a method employing two DNA capturing steps may be employed. In a first step, full DNA strands are captured prior to amplification. This first step may be non-specific and may use, for example, silica beads. In one embodiment, two types of DNA capturing probes are used: a first type captures the full DNA strands prior to the amplification, the second type captures the small DNA segments resulted from DNA amplification. After the sample is collected and introduced to the single chamber, DNAs are released by lysing at about 95° C. The first type of DNA probes, shown as 328 in FIG. 11 for example, capture the targeted DNAs, and unbound contaminants may then be removed from the chamber by flushing the chamber with washing fluid into a waste reservoir. The primers and enzymes are then introduced into the chamber and the captured DNAs are amplified at 63° C. for about 20 minutes. Then the second type of DNA capturing probes captures the small DNA segments resulted from the amplification.

The second type of DNA capturing probes may have multiple subtypes each of which targets a specific type of DNA segment associated with a specific pathogen. In some embodiments, each different subtype may target a DNA segment associated with each different pathogen. These subtypes of DNA capturing probes are coated at different locations of the chamber wall, shown as 331a, 331b, and 331c in FIG. 11 for example, thus different DNA segments are concentrated and immobilized at different locations of the chamber wall. This difference in location allows for ease of subsequent detection. During the detection step, the coloring dye mix is introduced and reacts with the specific DNA segments captured at different locations. Then, the device detects the bound dye at each location to obtain the positive or negative results for each pathogen or gene target. The detection methods may include but are not limited to colorimetric measurement and spectrum analysis. FIG. 11 illustrates a single chamber design for lysis and containing multiple nucleic acid capture sites to initiate amplification and multiple nucleic acid capture sites to capture amplified product for detection. In general, the first type of DNA probes (beads and/or wall coating) is located closer to where the sample swab is inserted, while the second type of DNA probes (beads and/or wall coating) are located closer to detection viewing windows or detection sensing components.

In one embodiment, the chamber can have a reading area for colorimetric display of results. This area may comprise for example a or multiple translucent or transparent windows forming a or part of the chamber wall or walls on which the capture probes are coated. Suitably, this window will have an internal surface on which the captures probes are coated and an external surface, which suitably may have indicia indicating to a user the pathogen location associated with each capture probe location. The external surface of the viewing window may for example be covered by an opaque layer having apertures therein corresponding to the location of the capture probes, wherein a calorimetric signal in such an aperture is indicative to a user of a positive result. Such an opaque layer, for example, can be part of a device enclosure holding the chamber or, for example, a sticker positionable over the viewing window. Alternatively, the external surface of the viewing window may have indicia printed thereon representative of the location of the capture probes and indicative to a user of a positive result with respect to a pathogen (e.g., but not limited thereto, a labelled grid system.) In one embodiment, the viewing window is suitably a magnifying window that facilitates visual reading of results. Part(s) or all of the window may be coloured or tinted to enhance the colour(s) of dye(s) used in detection. As discussed above, the device may include a control amplification and, accordingly, in one embodiment, the user may be provided with an indicia that the control was amplified and detected (i.e. an indicia that the device is functional and amplification of DNA was successfully performed).

In another embodiment, the coloring dyes are coated onto the single chamber. In this embodiment, a single set of capture probes may be used. The device detects the dye color change at each location to obtain the positive or negative results of each pathogen. The dye spots may be of the same type of dye or may be of different types (for example, identifiable as different colours.) In one embodiment, wherein screening is being performed for different nucleic acids, each primer set corresponding to each nucleic acid being screened may be labelled with a different molecular tag specifically complementary to a corresponding label on a given dye spot.

Table 1 provides oligonucleotide primers for isothermal amplification and detection of various viral and bacterial pathogens

TABLE 1

| Organism | Gene target | Amplification method | Primers (5' to 3') |
|---|---|---|---|
| Influenza A H3 | Matrix | LAMP | AGGATGGGGGCTGTAACC (SEQ ID NO: 1)<br>CCAGCCATTTGCTCCATAGC (SEQ ID NO: 2)<br>TGAGACCTGTGCTGGGAGTCAAGGTGGCATTGGCCTGGTA (SEQ ID NO: 3)<br>TAGGCAGATGGTGGCAACAACCTGTAGTGCTGGCCAAAACC (SEQ ID NO: 4)<br>AATCTGCTCACATGTTGCACA (SEQ ID NO: 5)<br>CATTAATAAAACATGAGAACAGAAT (SEQ ID NO: 6) |
| Influenza A H1 | Matrix | LAMP | CCGTTTTACTCGTGCCGC (SEQ ID NO: 7)<br>AGACGCTTTGTCCAAAATGC (SEQ ID NO: 8)<br>TCACAAGTGGCACACACTAG (SEQ ID NO: 9)<br>CCTTGGCCCCATGGAACGTTATGGGGACCCGAACAACATG (SEQ ID NO: 10)<br>TTCAACTGGTGCACTTGCCAGTGTGGTCACTGTTCCCATCC (SEQ ED NO: 11)<br>TGAGCTTCTTGTATAGTTTAACTGC (SEQ ID NO: 12)<br>TGCATGGGCCTCATATACAACA (SEQ ID NO: 13) |
| Influenza B | NS1 gene | LAMP | AGGGACATGAACAACAAAGA (SEQ ID NO: 14)<br>CAAGTTTAGCAACAAGCCT (SEQ ID NO: 15)<br>TCAGGGACAATACATTACGCATATCGATAAAGGAGGAAGTAAACACTCA (SEQ ID NO: 16)<br>TAAACGGAACATTCCTCAAACACCACTCTGGTCATAGGCATTC (SEQ ID NO: 17)<br>TCAAACGGAACTTCCCTTCTTTC (SEQ ID NO: 18)<br>GGATACAAGTCCTTATCAACTCTGC (SEQ ID NO: 19) |
| RSV A | Matrix | LAMP | GCTGTTCAATACAATGTCCTAGA (SEQ ID NO: 20)<br>GGTAAATTTGCTGGGCATT (SEQ ID NO: 21)<br>TCTGCTGGCATGGATGATTGGAGACGATGATCCTGCATCA (SEQ ID NO: 22)<br>CTAGTGAAACAAATATCCACACCCAGCACTGCACTTCTTGAGTT (SEQ ID NO: 23)<br>ACATGGGCACCATATTGTAAG (SEQ ID NO: 24)<br>AGGGACCTTCATTAAGAGTCATGAT (SEQ ID NO: 25) |
| RSV B | Pol gene | LAMP | AACCATTCCTGCTACAGAT (SEQ ID NO: 26)<br>CATCTTGAGCATGATATTTGC (SEQ ID NO: 27)<br>AGCATCGCAGACAAAGATACTAATCAACTAACAACATACATTGG TCT (SEQ ID NO: 28)<br>CCTGTCACAGCCAATTGGAGTCAGAAGAACAGTATTTGCACTT (SEQ ID NO: 29)<br>AACGCCGTCAACGACGTCGTGCCCTCGAGGACCTGCTC (SEQ ID NO: 30)<br>AGGTTCTGCAAATTTTATATGTAAATA (SEQ ID NO: 31) |
| *S. pyogenes* | DNase B gene | LAMP | TTCAATGACAGTCCCAACT (SEQ ID NO: 32)<br>GGTTTCCAGTCCATCCTG (SEQ ID NO: 33)<br>GCGTCCTTCCTAACTCATCTAATTTTTAGGTACTAGTCAGATTACTCC (SEQ ID NO: 34)<br>CTGCTAGAGGTACATTGACTTATGCCGGGGTTTTGATTTTTACCG (SEQ ID NO: 35)<br>TCCTGCTTTAGGAAAGAGTGCT (SEQ ID NO: 36)<br>CAATGTTGAAGGTAGCTACGGT (SEQ ID NO: 37) |

TABLE 1-continued

| Organism | Gene target | Amplification method | Primers (5' to 3') |
|---|---|---|---|
| S. aureus | Nuc gene | LAMP | CAAACCTAACAATACACATGAACA (SEQ ID NO: 38)<br>ACGCTAAGCCACGTCCATAT (SEQ ID NO: 39)<br>CGTTGTCTTCGCTCCAAAT (SEQ ID NO: 40)<br>TGCAAAGAAAATTGAAGTCGA (SEQ ID NO: 41)<br>TCAAGGCTTGGCTAAAGTTGCTTATTCGCTTGTGCTTCACTT (SEQ ID NO: 42)<br>CGTTTACCATTTTTCCATCAGCATATTTGACAAAGGTCAAAGAACT (SEQ ID NO: 43) |
| HSV1 | UL3 gene | EXPAR | CTGGCGATAT (SEQ ID NO: 44)<br>ATATCGCCAG (SEQ ID NO: 45)<br>ATATCGCCAGGTGAGACTCTATATCGCCAG (SEQ ID NO: 46)<br>CTGGCGCTTGATGGTATCCAGACTCTATATCGCCAG (SEQ ID NO: 47) |
| M. tuberculosis | gyrB | EXPAR | GAGTCCAGTATTTGGTCGTCTGTCCTGCGTAGCGACTC (SEQ ID NO: 48)<br>ATTTGGTCGTCGCAGACTCATTTGGTCGT (SEQ ID NO: 49)<br>ACCGGGCAGATTCGGCCCACTTCCCGCAGACTCATTTGGTCGT (SEQ ID NO: 50)<br>TTTTTTTTTACCGGGCAGATT (SEQ ID NO: 51)<br>CGGCCCACTTCCTTTTTTTT (SEQ ID NO: 52)<br>biotin-sp18-AATCTGCCCGGTAAAA (SEQ ID NO: 53) |
| Influenza H5 | HA gene | SMART | TCAAGAGTAGACACAGGATCAGCATAGGCAATAGATGG<br>AGTCACGTAATCAGATCAGAGCAATAGGTCA (SEQ ID NO: 54)<br>ATGGTAGATGGTTGGTATGGGTA (SEQ ID NO: 55)<br>CGTAGGCAATAGATGGAGTCACTACG (SEQ ID NO: 56)<br>AATTCTAATACGACTCACTATAGGGAGAAGGTGACCTATTGCTCTGATCTGATTAC (SEQ ID NO: 57)<br>TAATACGACTCACTATAGGTGACCTATTGCTCTGATCTGATTAC<br>TCAAGAGTAGACACAGGATCAGCAT (SEQ ID NO: 58) |
| Influenza H5 | HA gene | RCA | (PLP)GGATGATCTGAATTTTCTCAAACCCGGTCAACTTCAAGCTCCTAAGCCTTGACGAA (SEQ ID NO: 59)<br>GCTTAGGAGCTTGAAGTTG*A*C (SEQ ID NO: 60)<br>GCTTTGCCTGACTGAATGC*A*G (SEQ ID NO: 61) |
| H. pylori | ureC | HAD | CTTTTAGGGGTGTTAGGGGT (SEQ ID NO: 62)<br>AAGCTTACTTTCTAACACTAACGC (SEQ ID NO: 63)<br>CGATTGGGGATAAGTTTGTG (SEQ ID NO: 64) |
| S. aureus | mecA | RPA | TCCAACATGAAGATGGCTATCGTGICACAATCGTT (SEQ ID NO: 65)<br>CCTGTTTGAGGGTGGATAGCAGTACCTGAGCC (SEQ ID NO: 66) |
| S. enterica | invA | RPA | TACCGGGCATACCATCCAGAGAAAATCGGGCCGC (SEQ ID NO: 67)<br>ATTGGCGATAGCCTGGCGGTGGGTTTTGTTGT (SEQ ID NO: 68) |
| S. epidermidis | gse A | LAMP | AACATCACTGTTACTGGTTAC (SEQ ID NO: 69)<br>CTGCTATTGTATTTATTATCTACGC (SEQ ID NO: 70)<br>CTCGCCACCAATATAGACAACTTTTGGTGACAAACCATTAGCC (SEQ ID NO: 71)<br>GACCTAAGTACTGTAGGTGGAAACTCACCATAATGTATTCCAATAACTTG (SEQ ID NO: 72) |

Primers exemplified in Table 1 have been used in accordance with the following references which are incorporated herein by reference:

[1] Mahony J. et al. 2013; J Clin Virol 2013 58:127-131.
[2] Mahony J. et al. 2013; J. Clin. Microbiol. 2013 doi: 10.1128/JCM.00662-13.
[3] Deguo Wang and Yanhong Liu Int. J. Environ. Res. Public Health 2015, 12, 5735-5742; doi:10.3390/ijerph120605735
[4] Wang D. et al. Molecules 2015 20, 9487-9495
[5] Tan E. et al. 2007; Clin Chem 53(11) 2017-2020.
[6] Roskos K. et al. 2013; PLOS One 8(7):e69355.
[7] McCalla et al. 2012; J Molec Diagn 14(4):328-335.
[8] Hamidi S. et al. 2015; Analyst 140, 1502-1509.
[9] Gill P. et al. 2007; Diagn Microbiol Infect Dis 59:243-249.
[10] Kersting S. et al. 2014; Microchim Acta 181:1715-1723.

Thus, in one embodiment, the device is a stand-alone device that requires no outside equipment for reading results. However, in some embodiments, the device may be adapted for connection to a device for transmitting or displaying results, as discussed further below.

The detection sensor of the device may be adapted for connection to a signal processing unit operable to receive the signal provided by the detection sensor and to translate the signal into a desired output. Thus, the signal processing unit is operable to digitize the output provided by the detection sensor, if required, into a recordable output which may be presented, for example, on a display, e.g. monitor or the like. For example, in one embodiment, the results of the diagnostic assay can be transmitted to an on-board intelligent reader for the user to view results. The signal processing unit may be included within the device in the form of a microprocessor (e.g. digital signal processor) including any required convertors to translate the output from the detection sensor (analog to digital convertor), or in the form of a digital acquisition board to digitize the signal from the detection sensor. Alternatively, the signal processing unit may be an external processing system. In such an embodiment, the device is equipped with a port for communication with an external processing system. The port may be a physical port (e.g. a USB port) which may function to transfer power to the device from the external processing system, and to transfer output from the detection sensor to the external processing system for signal processing. Alternatively, the port may be a wireless communication port, for example using the WiFi or Bluetooth protocols, which functions to transfer output from the detection sensor to the external processing system for signal processing. Examples of external processing systems include personal computers, personal digital assistants, networked mobile wireless telecommunication computing devices such as smartphones, and content players.

Aspects of the present technology used to implement the signal processing unit may be embodied within a system, a method, a computer program product or any combination thereof. The computer program product may include a computer readable storage medium or media having computer readable program instructions thereon for causing a processor to carry out aspects of the present technology. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technology may be assembler instructions, instruction-set-architecture (ISA) instructions, machine instructions, machine dependent instructions, microcode, firmware instructions, state-setting data, or either source code or object code written in any combination of one or more programming languages, including an object oriented programming language or a conventional procedural programming language. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to implement aspects of the present technology.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 7:
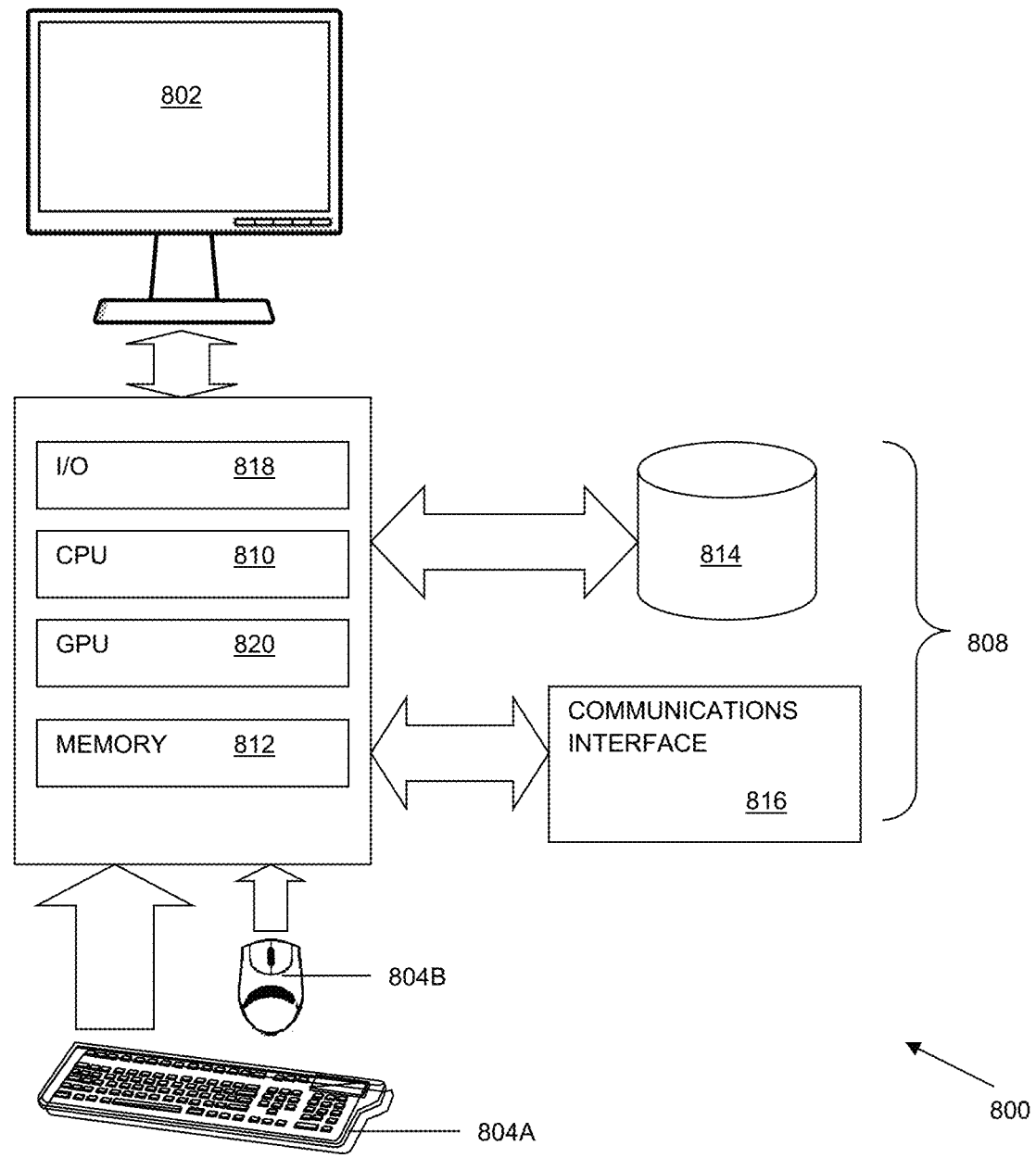
FIG. 7 is a block diagram showing an exemplary computer system which may be used to implement aspects of the present technology.

An illustrative computer system in respect of which aspects of the technology herein described may be implemented (e.g. which may function as a signal processing unit) is presented as a block diagram in FIG. 7. The illustrative computer system is denoted generally by reference numeral 800 and includes a display 802, input devices in the form of keyboard 804A and pointing device 804B, computer 806 and external devices 808. While pointing device 804B is depicted as a mouse, it will be appreciated that other types of pointing device may also be used. INcomputer 806 may contain one or more processors or microprocessors, such as a central processing unit (CPU) 810. The CPU 810 performs arithmetic calculations and control functions to execute software stored in an internal memory 812, preferably random access memory (RAM) and/or read only memory (ROM), and possibly additional memory 814. The additional memory 814 may include, for example, mass memory storage, hard disk drives, optical disk drives (including CD and DVD drives), magnetic disk drives, magnetic tape drives (including LTO, DLT, DAT and DCC), flash drives, program cartridges and cartridge interfaces such as those found in video game devices, removable memory chips such as EPROM or PROM, emerging storage media, such as holographic storage, or similar storage media as known in the art. This additional memory 814 may be physically internal to the computer 806, or external as shown in FIG. 7, or both.

The computer system 800 may also include other similar means for allowing computer programs or other instructions to be loaded. Such means can include, for example, a communications interface 816 which allows software and data to be transferred between the computer system 800 and external systems and networks. Examples of communications interface 816 can include a modem, a network interface such as an Ethernet card, a wireless communication interface, or a serial or parallel communications port. Software and data transferred via communications interface 816 are in the form of signals which can be electronic, acoustic, electromagnetic, optical or other signals capable of being received by communications interface 816. Multiple interfaces, of course, can be provided on a single computer system 800.

Input and output to and from the computer 806 is administered by the input/output (I/O) interface 818. This I/O interface 818 administers control of the display 802, keyboard 804A, external devices 808 and other such components of the computer system 800. The computer 806 also includes a graphical processing unit (GPU) 820. The latter may also be used for computational purposes as an adjunct to, or instead of, the (CPU) 810, for mathematical calculations.

The various components of the computer system 800 are coupled to one another either directly or by coupling to suitable buses.

Figure 8:
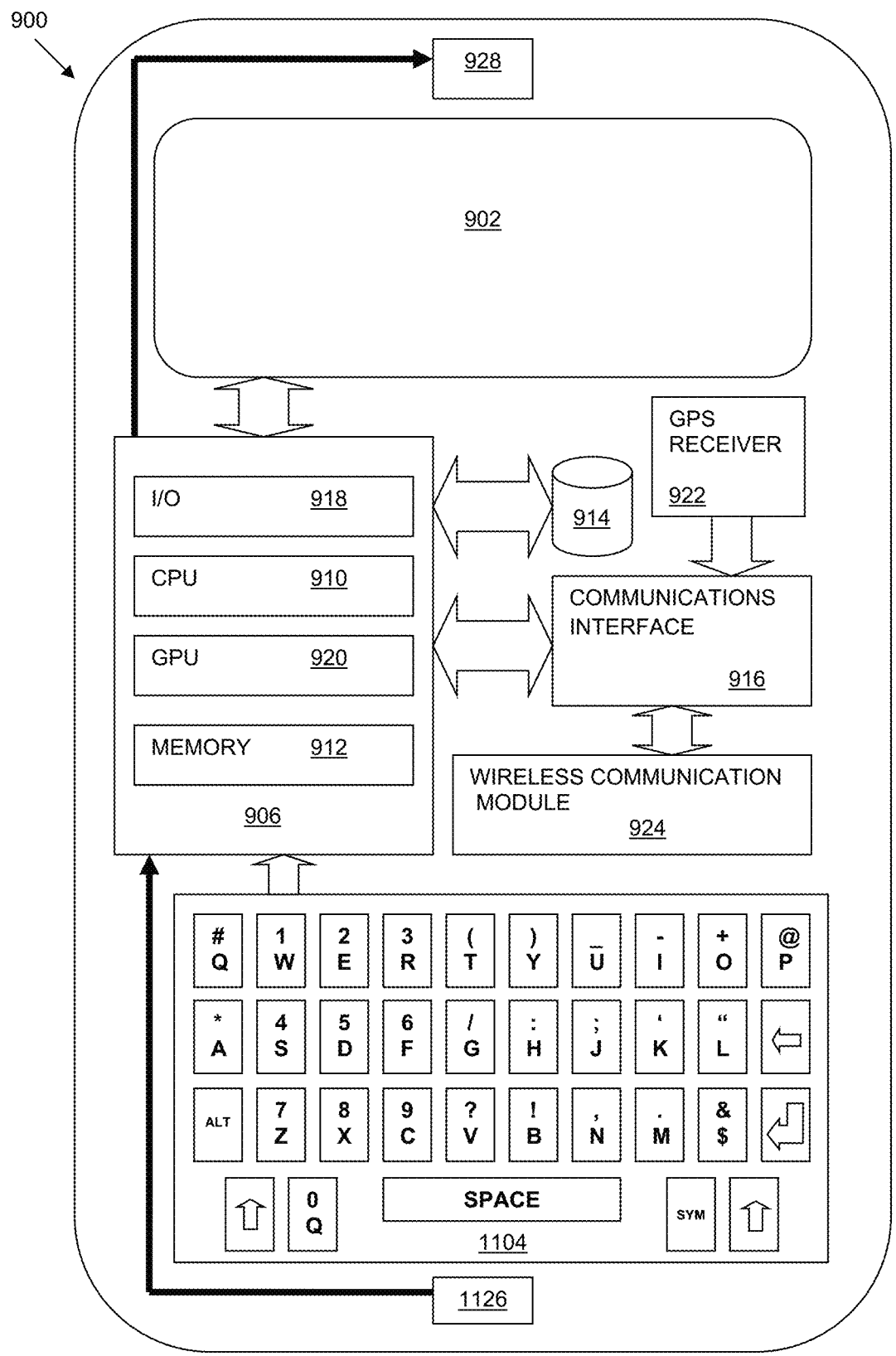
FIG. 8 is a block diagram showing an exemplary smartphone which may be used to implement aspects of the present technology.

In another embodiment, the results can be interpreted using a networked mobile wireless telecommunication computing device such as a smartphone programmed with a specific application for interpreting results. FIG. 8 shows an exemplary networked mobile wireless telecommunication computing device in the form of a smartphone 900; the smartphone 900 which may function as a signal processing unit. The smartphone 900 includes a display 902, an input device in the form of keyboard 904 and an onboard computer system 906. The display 902 may be a touchscreen display and thereby serve as an additional input device, or as an alternative to the keyboard 904. The onboard computer system 906 comprises a central processing unit (CPU) 910 having one or more processors or microprocessors for performing arithmetic calculations and control functions to execute software stored in an internal memory 912, preferably random access memory (RAM) and/or read only memory (ROM) is coupled to additional memory 914 which will typically comprise flash memory, which may be integrated into the smartphone 900 or may comprise a removable flash card, or both. The smartphone 900 also includes a communications interface 916 which allows software and data to be transferred between the smartphone 900 and external systems and networks. The communications interface 916 is coupled to one or more wireless communication modules 924, which will typically comprise a wireless radio for connecting to one or more of a cellular network, a wireless digital network or a Wi-Fi network. The communications interface 916 will also typically enable a wired connection of the smartphone 900 to an external computer system. A microphone 926 and speaker 928 are coupled to the onboard computer system 906 to support the telephone functions managed by the onboard computer system 906, and GPS receiver hardware 922 may also be coupled to the communications interface 916 to support navigation operations by the onboard computer system 906. Input and output to and from the onboard computer system 906 is administered by the input/output (I/O) interface 918, which administers control of the display 902, keyboard 904, microphone 926 and speaker 928. The onboard computer system 906 may also include a separate graphical processing unit (GPU) 920. The various components are coupled to one another either directly or by coupling to suitable buses.

The term "computer system" and related terms, as used herein, are not limited to any particular type of computer system and encompasses servers, desktop computers, laptop computers, networked mobile wireless telecommunication computing devices such as smartphones, tablet computers, as well as other types of computer systems.

Thus, computer readable program code for implementing aspects of the technology described herein may be contained or stored in the memory 912 of the onboard computer system 906 of the smartphone 900 or the memory 812 of the computer 806, or on a computer usable or computer readable medium external to the onboard computer system 906 of the smartphone 900 or the computer 906, or on any combination thereof.

Thus, in one embodiment of the device, diagnostic results are sent to a smartphone, laptop or any suitable computing device using either a wired or wireless connection. The computing device will include software that can interpret and present the diagnostic information for the user. In addition, the PON diagnostic platform can be powered using an on-board battery source, through a DC power adaptor, or by a smartphone, computer or other device through a USB or other suitable connection.

In another embodiment of the device, an on-board reader will be available that will directly analyze/interpret/display the POCT result for the user.

In one embodiment, each device will include a Radio Frequency Identification (RFID) tag to allow for tracking and data analysis.

As mentioned above, preferably devices of the present invention are disposable. In one embodiment, the materials used to manufacture devices of the present invention are not particularly restricted and include e.g. glass, silica, silicon and other materials. However, in various embodiments, the devices are manufactured at least in part from plastics or other polymers, which may be biodegradable. The devices may also include metal components in particular, but not restricted to, in relation to heating components. Methods for manufacturing microfluidic devices are known and, in particular, processes of hot embossing to manufacture plastic microfluidic devices are known.

Potential Applications

A disposable, inexpensive POC device is provided which has applications across a broad range of disciplines and sectors. At the outset, the device is advantageously made to be disposable to keep manufacturing costs manageable, to avoid the necessity of cleaning the device after use, and to avoid spread of possible pathogenic infection by further handling of a used device. Following use, the device may be disposed of using protocols established to avoid spread of infection.

One use of this POC device is the rapid detection of pathogenic microorganisms. For example, the POC device may be used to detect pathogenic microorganisms such as, but not limited to, *Escherichia coli, Listeria monocytogenes, Clostridium difficile, Mycoplasma pneumonia, Chlamydia pneumoniae, Chlamydia trachomatis, Legionella pneumophilia, Neisseria gonorrhea, Streptococcus, Staphylococcus,* Influenza virus, Respiratory Syncytial Virus, Norovirus, West Nile Virus, Dengue Virus, SARS Co-V, Ebola virus, Lassa fever virus, Tuberculosis, HIV or Middle East respiratory syndrome coronavirus.

Thus, the present POC device is particularly useful to detect infectious diseases in resource-poor settings without access to a central laboratory for molecular testing. For example, this device can be used to detect infectious disease in Africa, e.g. diarrheal disease using rectal swabs, or HIV. The POC device is useful for testing surfaces in food-processing plants for *Listeria* or *E. coli* contamination. The POC device can be used for real-time contamination monitoring in food-processing plants and to ensure sterilization during cleaning processes, and to prevent food-associated outbreak of gastrointestinal diseases. Another application of the POC device is the detection of disease in animals, such as porcine-respiratory virus in pigs by veterinarians, which severely affects the porcine industry. This device can also be used to prevent nosocomial or hospital-acquired infections in Emergency departments or waiting rooms in hospital and in other clinical settings including nursing and old-age homes, and walk-in clinics. Another application of this device is for at-home testing for sexually transmitted infections including *Chlamydia trachomatis*. Women can take a vaginal swab, which is highly sensitive for *Chlamydia* detection, and use this POC device to test the vaginal swab for *C. trachomatis*. This device can also be used for real-time surveillance and outbreak control in large populations. In addition, it can be used to respiratory virus testing for passengers embarking or disembarking airplanes.

Another use of the device is in detecting antibiotic or antiviral resistance. Genes conferring resistance are known and include, for example, the betalactamase gene conferring penicillin resistance, ESBLs and carbapenemase, the MCR-1 gene conferring colistin resistance. These genes may be amplified according to methods and using devices as described above. The device can be used to test both for the presence of the bacteria and for the specific gene conferring resistance. In one embodiment, the device can be used to test for rifampicin resistant tuberculosis.

Another use of this POC device is the rapid detection of biomarkers for diseases including but not limited to breast cancer, lung cancer, colorectal cancer, diabetes, coronary heart disease, chronic obstructive pulmonary disease, hepatitis, kidney disease, Multiple sclerosis, Alzheimer's disease, and Parkinson's disease. Molecular biomarkers can include either specific mRNA transcripts or micro RNAs. The POC device for molecular biomarkers of disease would be either a multiple channel or single channel device as described above or in the Examples below. Specific primers for the amplification of mRNA or micro RNA species would be included in the amplification mixture. Amplification and detection would be the same as for the POC device for detecting infectious agents.

As will be apparent to a person of skill in the art, the device may be similarly used in veterinary applications.

Embodiments of the invention are described in the following specific example, which is not to be construed as limiting.

Example 1—a PON Device for Pathogen Detection

Device Design

A hand-held, disposable device 10 is provided (FIG. 1B). The device 10 comprises a first extraction chamber 12 having a maximum volume of about 250 µl. The extraction chamber 12 includes a lysing reagent of PBS with 0.1% Triton X-100. The extraction chamber 12 includes an opening 11 for accepting the head of a sample-containing swab and the chamber 12 is sized to accept the swab. A lid 13 is provided to seal opening 11 of the extraction chamber 12. Closing of lid 13 activates the device 10 by causing release of buffer into the extraction chamber 12 from a blister pack. The extraction chamber 12 is fitted with a first self-regulating heater 14, activated on closing lid 13, that heats the extraction chamber 12 to a temperature of about 95° C. and maintains this temperature for at least 2 minutes, e.g. by the use of a timer. The heater 14 is connected to control unit 30 and powered by battery 34.

The extraction chamber 12 is connected by a microfluidic channel 16 to an amplification chamber 20. A pump means 18, e.g. a micropump, is located within the microfluidic channel 16 and functions to move lysed material from the extraction chamber 12 to the amplification chamber 20. The pump 18 is connected to control unit 30 and powered by battery 34. The control unit also includes a D/A converter 15 for temperature and/or potential controls, and an A/D converter 25 to convert analogue detection signals to digital signals. A timer activates the pump 18 at the appropriate time. The amplification chamber 20 includes a second self-regulating heater 22, activated by a timer as described, which maintains the temperature within the amplification chamber 20 at 55-70° C. for 20 minutes to allow for isothermal amplification, including loop-mediated isothermal amplification (LAMP), cross-priming amplification (CPA), recombinase polymerase amplification (RPA), rolling circle amplification (RCA), helicase-dependent amplification (HDA), single-mediated amplification of RNA technology (SMART), nicking enzyme-mediated amplification (NEMA), isothermal chain amplification (ICA), Smart amplification (Smart-AMP), exponential amplification reaction (EXPAR), ramification amplification (RAM), nicking end amplification reaction (NEAR) or PCR.

Once the lysed material is cooled to the target temperature of about 63° C. over time, between 5 and 10 µl of lysed material is transferred to the amplification chamber 20 by pump 18. The lysed material is maintained at about 62° C. with a second self-regulating heater 24 within the amplification chamber. The second heater 24 is connected to control unit 30 and powered by battery 34. The amplification chamber contains an amplification master mixture of salt buffer, DNA polymerase, 5 mM $MgSO_4$, and target-specific primers, e.g. 15 µl of salt buffer solution, 1 µl of polymerase, and 4 µl of specific primers, with 5 to 10 µl of DNA binding dye (Quant-iT PicoGreen, hydroxynapthol blue, and leuco triphenylmethane dye).

The amplification chamber 20 contains a detection sensor 26, which could be a colorimeter for RGB analysis, a fluorimeter to detect fluorescence changes after amplification with a fluorescent dye, a potentiometer to perform electrochemical analysis of the sample with methylene blue, or a clear viewing port to analyze a visual colour change.

In an alternate embodiment illustrated in FIG. 1A, the amplification chamber 20 is connected to a separate detection chamber 50, via a microfluidic channel 28, and the detection chamber 50 includes the detection sensor 26.

Lysis Validation

To confirm that the extraction chamber could reach a target temperature (95° C.) using a self-regulating heater and maintain this temperature for two to three minutes, the temperature was monitored for 20 minutes using a thermocouple. Different resistances (3.8 ohm, 3.5 ohm, and 3.4 ohm) were tested. All measurements were performed in a tinfoil chamber attached to the PTC heater coupled with a thermal paste. To further confirm that these conditions were sufficient to lyse various clinical samples, swabs containing Respiratory Syncytial Virus A (RSV-A), *Streptococcus pyogenes*, and Influenza virus H1 were each placed within the extraction chamber containing 250 µl of PBS with 0.1% Triton-X100 and lysed for 3 minutes followed by amplification using the amplification mix, Optigene Lamp mastermix, on the fluorimeter, the Genie II instrument. Amplification times were compared with an unlysed control in each case. Oligonucleotide primers from Table 1 used in each case were as follows: primers for RSV-A having SEQ ID NOs: 20, 21, 22, 23 and 24), primers for *Streptococcus pyogenes* having sequences of SEQ ID NOs: 32, 33, 34, 35, and 36, and primers for Influenza virus H1 having sequences of SEQ ID NOs: 7, 8, 9, 10 and 11.

Amplification Validation

To confirm that the amplification chamber 20 reached the required temperature (63° C.) and maintained this temperature for 20 minutes, a thermistor was used to monitor the chamber 20 temperature over time. Using a constant resistance of 8.6 ohm, the temperature was monitored for 20 minutes. To further confirm that the samples were successfully amplified under these conditions, RSV-A, *S. pyogenenes*, and influenza virus H1 were heat-lysed on a heat-block at 95° C. for 10 minutes and amplified in the amplification chamber 20 containing 15 µl of Optigene mastermix and 5 µl of specific primers as described above for 15 minutes. The sample was then removed from the amplification chamber, mixed with 10 µl of SYBR Green DNA binding dye, and end-point fluorescence at between 500 and 520 nm was determined on the Genie II instrument compared to an unamplified negative control.

Detection Validation

To evaluate whether amplified DNA could be detected either visually or using electrochemical detection, a variety of DNA binding dyes including Quant-iT PicoGreen (Life Technologies), hydroxynapthol blue, leuco triphenylmethane dye, and methylene blue were used. Approximately 100 copies of either RSV-A, *S. pyogenes*, or influenza virus H1 were amplified using the amplification mixture including primers as described above, Optigene LAMP mastermix, after which the amplified material was mixed with 10 µl of individual DNA binding dyes for 3 minutes at room temperature. For Quant-iT PicoGreen, hydroxynapthol blue, and leuco triphenylmethane dye, a visual change in the colour of the dye was observed by at least 10 individuals. For methylene blue, detection was achieved based on changes in the peak anodic current in the sample using cyclic voltammetry with a PalmSens potentiostat and compared to a baseline reading prior to amplification.

Nucleic Acid Capture Validation

Figure 12:
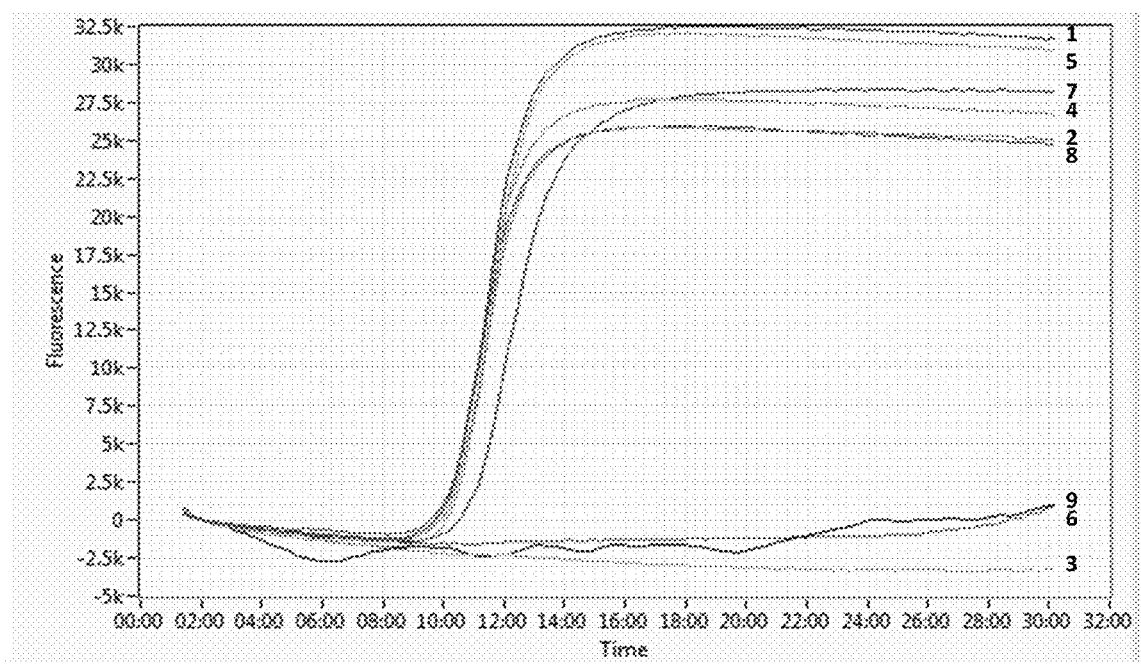
FIG. 12 shows amplification and detection of targets in stool specimens following removal of amplification inhibitors by either total nucleic acid capture or specific target capture.

To confirm that nucleic acid could be captured by immobilized oligonucleotide capture probes an aliquot (0.1 mL) of a clinical specimen (for example, a stool or urine sample or a sample containing *S. pyogenes*) was mixed with 10 µL of biotinylated capture probe and heated for 10 minutes at 95° C. The sample was cooled to room temperature and an aliquot of Streptavidin-coated magnetic beads (10 µL) were added and the mixture was left for 5 minutes at room temperature. The beads were removed with a magnet, then re-suspended in 20 µL PBS and 5 µL was tested by LAMP in the Genie II real-time fluorometer and compared to a negative specimen. FIG. 12 shows the removal of amplification inhibitors from three stool specimens using either total nucleic acid capture on magnetic silica dioxide beads or using specific target capture using a biotin-labled oligonucleotide probe bound to streptavidin-coated micro beads. Table 2 shows that amplification occurs following nucleic acid capture and removal of inhibitors. Influenza A virus was spiked into the samples.

TABLE 2

| | Flu A LAMP Amplification Time (mm:ss), Annealing Temperature (° C.) | | |
|---|---|---|---|
| | Target Captured DNA (magnetic silica beads) | Target Captured DNA (biotin primer) | Heating without removal of inhibitors |
| Sample 1 + Spike | 11:00, 86.43 | 11:00, 86.43 | — |
| Sample 2 + Spike | 10:45, 86.03 | 11:15, 86.55 | — |
| Sample 3 + Spike | 11:45, 86.61 | 10:45, 86.55 | — |

Figure 13:
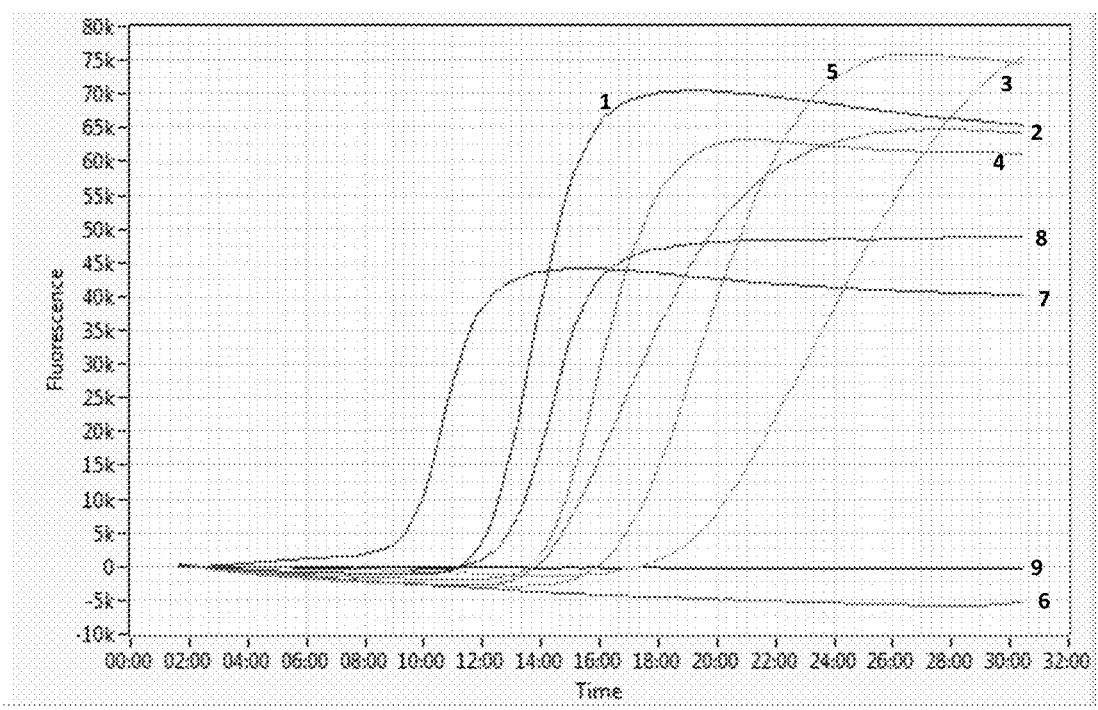
FIG. 13 shows amplification and detection of targets in urine specimens following removal of amplification inhibitors by either total nucleic acid capture or specific target capture.

FIG. 13 and Table 3 shows the complete removal of amplification inhibitors from two urine specimens (sample 2 and 3) and partial removal from a third urine specimen (sample 1) using either total nucleic acid capture using the easyMAG extractor (NucliSENS easy Mag® bioMerieux) or using specific target capture using a biotin-labled oligonucleotide probe bound to streptavidin-coated micro beads. *Streptococcus agalactiae* (Group B Strep) was spiked into the urine specimens.

TABLE 3

| | GBS LAMP Amplification Time (mm:ss), Annealing Temperature (° C.) | | |
|---|---|---|---|
| | easyMAG Extracted DNA | Target Captured DNA (magnetic silica beads) | Heating without removal of inhibitors |
| Sample 1 | 12:45, 81.77 | 15:00, 81.91 | 20:15, 82.26 |
| Sample 2 | 14:45, 81.67 | 18:00, 82.11 | — |
| Sample 3 | 10:00, 82.20 | 13:30, 82.10 | — |

See FIG. 12: Removal of amplification inhibitors from three stool samples using either total nucleic acid (silica beads) or specific target capture (biotinylated oligo) permits amplification. Line 1, Sample 1—Target Capture with Silica Beads, Line 2-Sample 1—Target Capture with Biotin Primer; Line 3-Sample 1—Heating Only; Line 4-Sample 2—Target Capture with Silica Beads; Line 5-Sample 2—Target Capture with Biotin Primer; Line 6-Sample 2—Heating Only; Line 7-Sample 3—Target Capture with Silica Beads; Line 8-Sample 3—Target Capture with Biotin Primers; Line 9-Sample 3—Heating Only; and FIG. 13: Removal of amplification inhibitors from three urine samples using either total nucleic acid (silica beads) or specific target capture (biotinylated oligo) permits amplification (specimens 2 and 3) or increases time to positivity (specimen 1). Line 1, Sample 1—easyMAG Extracted DNA; Line 2, Sample 1—Target Capture with Silica Beads; Line 3, Sample 1—Heating Only; Line 4, Sample 2—easyMAG Extracted DNA; Line 5, Sample 2—Target Capture with Silica Beads; Line 6, Sample 2—Heating Only; Line 7, Sample 3—easyMAG Extracted DNA; Line 8, Sample 3—Target Capture with Silica Beads; Line 9, Sample 3—Heating Only.

Sample Analysis

Approximately 500 S. pyogenes bacterial cells, RSV-A particles, or influenza particles H1 were applied to respective nasopharyngeal swabs to mimic a clinical swab sample from an infected patient. The swab was placed in the extraction or extraction chamber 12 of a device 10. The extraction chamber 12 contained 250 µl of phosphate buffer saline and 0.1% Triton X-100, which was subsequently heated to 95° C. using a self-regulated heating device. This temperature was maintained for 3 minutes, after which 25 µl of the lysed solution was transferred to the amplification chamber 22 of the device 10 using a pipette. The 25 µl of lysed solution was mixed with LAMP amplification buffer containing a strand-displacement DNA polymerase from B. stereothermophius (Bst 2.0 New England Biolabs), primers (5 µl total) targeting a specific S. pyogenes, RSV-A, or influenza H1 gene (as described above), 5 µl of dNTPs, 1 µl of $MgSO_4$, and 15 µl of a salt-buffer at pH 9.2. The amplification chamber 22 was maintained at 63° C. using a self-regulated heater for 20 minutes to allow amplification to occur. Amplification was monitored using a fluorescent dye (10 µl of SYBR green), and amplification was detectable within 14 minutes. Total time to detect S. pyogenes from a clinical swab was 19 minutes, which included a 5 minute sample release and lysis step.

Electrochemical detection of DNA amplification was also used. After incubation for 20 minutes at 63° C. in the amplification chamber 22, the sample was analyzed using methylene blue detection and cyclic voltammetry with a PalmSens potentiostat and compared to a baseline reading taken prior to amplification. Decrease in peak anodic current is indicative of amplification. Methylene blue (MB) at two different concentrations was used to detect 500 ng of amplified DNA. Methylene blue alone was used as a control.

Analysis of Self-Regulated Heating

Figure 2:
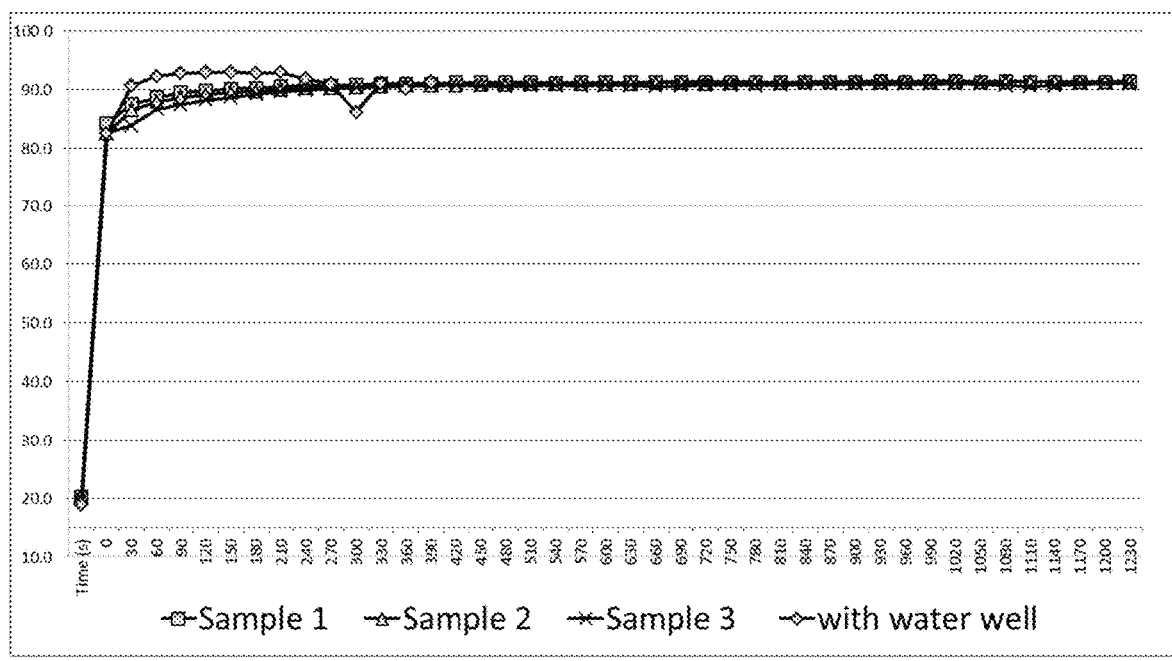
FIG. 2 graphically illustrates that a self-regulated heater could heat 250 µl of water to 95° C. at different resistances (3.8 ohm, 3.5 ohm, and 3.4 ohm) for 20 minutes by applying a voltage.
Figure 3:
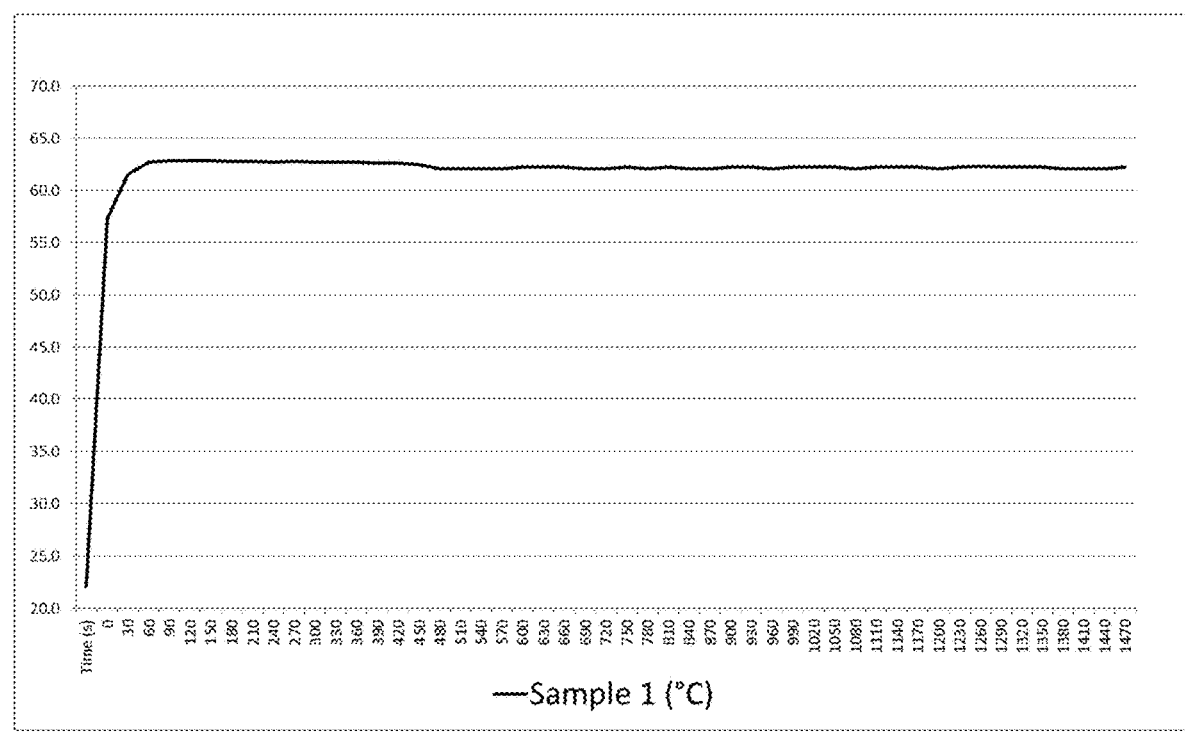
FIG. 3 graphically illustrates that a self-regulated heater could heat 250 µl of water to 63° C. at a resistance of 8.6 ohms by applying a voltage.

Accurate temperature control was confirmed in the device 10 for lysis of infectious materials and for amplification of DNA. Self-regulating heaters to maintain temperature in the extraction chamber at 93° C. and in the amplification chamber at 63° C. were used. For the lysis temperature, various resistances were tested to explore whether the self-regulating heater could function appropriately under various conditions at room-temperature. It was found that the temperature of 93° C. was maintained for over 20 minutes at all resistances tested (FIG. 2). For the amplification temperature, a temperature of 63° C. could be maintained at 8.6 ohm for 20 minutes (FIG. 3). Based on these results, the self-regulating heaters were determined to be sufficient to maintain temperatures for lysis and amplification.

Evaluation of Sample Lysis

To confirm that the device 10 was sufficient to lyse clinical material and sterilize clinical specimens within 3 minutes at 93° C., Respiratory Syncytial Virus (RSV), Influenza, E. coli, and S. pyogenes were separately introduced into the extraction chamber 12 of the device 10 for subsequent analysis. It was first determined that virus and bacteria were killed in the extraction chamber 12, to ensure that the device is not a biohazard after being used. To accomplish this, 10,000 bacterial or viral particles were introduced into the extraction chamber, were lysed and then were analyzed either based on a plating assay (for bacteria) or through infection and cell culture (for viruses). No viable (infectious) pathogens remained after exposure to the extraction chamber 12, indicating that exposure to 93° C. for 3 minutes kills 100% of the virus or bacteria. It was then determined that these conditions released intracellular DNA and RNA that could be used for DNA amplification. Following lysis of each sample, the resulting DNA or RNA was analyzed using LAMP on a Genie II instrument compared to a positive lysis control (bead lysis). It was found that LAMP could detect released nucleic acid from all four specimens, suggesting that the extraction chamber could be used to release nucleic acid for subsequent analysis.

Evaluation of Isothermal DNA Amplification In Situ

Figure 4:
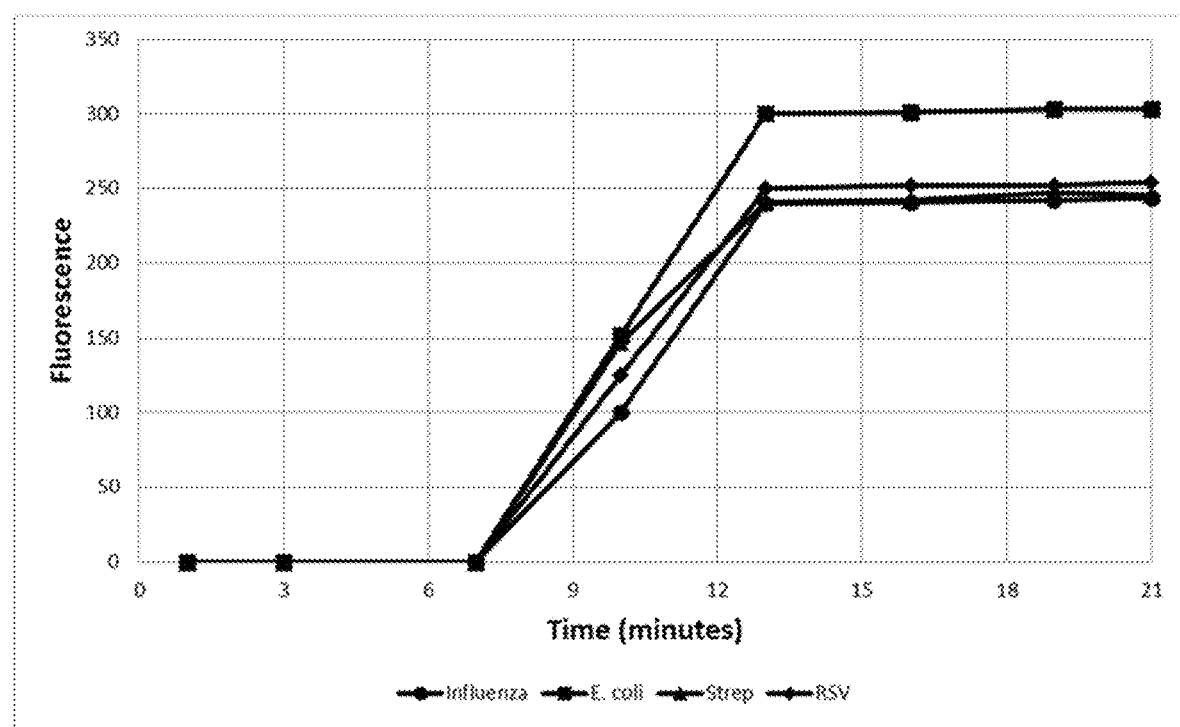
FIG. 4 graphically illustrates detection of Influenza A, RSV, E. coli and S. pyogenes following amplification, using a fluorescent dye (SYBR Green).

To confirm that isothermal amplification could be performed in the device 10, RSV, Influenza, E. coli, and S. pyogenes samples were bead lysed and amplified within the amplification chamber 22. The samples were subsequently analyzed based on end-point fluorescence with Sybr Green DNA binding dye. All specimens were amplified in the chamber within 10 minutes (FIG. 4).

DNA Detection In Situ

Figure 6:
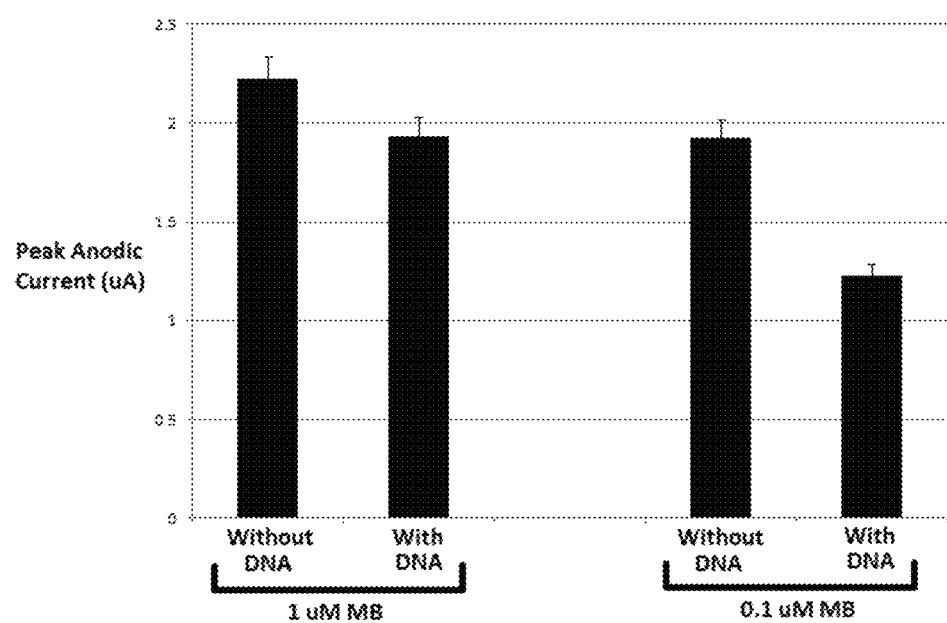
FIG. 6 graphically illustrates electrochemical detection of amplified S. pyogenes DNA using methylene blue at 2 concentrations and measuring peak anodic current.

Detection of DNA was performed using both a visual color using Quant-It PicoGreen DNA binding dye and through potentiometry using Methylene Blue. To accomplish this, amplified DNA was mixed with either Quant-It PicoGreen or Methylene Blue dye and analyzed either visually or using potentiometry, respectively. For visual detection, color change in the presence of amplified DNA, and lack of color change in the absence of amplified DNA, was detectable by the naked eye or electronics colorimetric detection by RGB analysis (FIG. 5). For DNA detection using methylene blue (MB), peak anodic current in the presence and absence of amplified DNA was determined. A significant decrease in the peak anodic current of 20 to 25% was observed in the presence of amplified DNA (FIG. 6). At lower MB concentrations (0.1 µM, there was a greater decrease in peak anodic current compared to higher MB concentrations (1 µM) in the presence of amplified DNA making this lower concentration preferred.

Example 2

Clinical Analysis

The device 10 was tested using clinical Influenza-positive nasopharyngeal swabs, RSV-positive nasopharyngeal swabs, and S. pyogenes-positive throat swabs. Swabs were obtained from infected patients that were known to be positive based on culturing methods. The swabs were then inserted into the extraction chamber 12 of the device 10. The extraction chamber was filled with 250 µl of PBS and heated at 93° C. for 3 minutes. Subsequently, the lysed material was pumped into the amplification chamber 22, where it was mixed with LAMP master mix. The amplification chamber 22 was then activated for 15 minutes (heated to 63° C.) and DNA was detected visually after mixing with Quant-It PicoGreen DNA binding dye in the viewing windows (vials in FIG. 1c). Pathogens were detected within 20 minutes using the device.

Example 3

An example embodiment of the hand-held, disposable device is shown in the photograph of FIG. 1C, incorporating key functional modules and structures described herein. Sample extraction and Lysis were both carried out within extraction/lysing chamber 12', while DNA amplification and viewing/detection were carried out in the subsequent amplification chambers 20 connected by microfluidic channels 16, and detection chambers 50 for displaying results. In this example, the extraction/lysing chamber 12' is adapted to accept the swab at swab insertion point 9. This embodiment incorporates one (1) extraction/lysing chamber 12' constructed with metal alloy material, two parallel amplification chambers 20 constructed with metal alloy material, two parallel microfluidic channels 16 and two detection chambers 50 constructed with polymer material. Therefore, this embodiment device is capable of detecting two different indications from the same sample swab or detecting one indication and one control reading. The extraction/lysing chamber 12 and the amplification chambers 20 are each bonded with one self-regulating heater, which are operated at 93° C. for lysing and 63° C. for amplification respectively. The implementation of the self-regulating heater does not require electronics control circuit (such as thermal sensor, microcontroller etc.), which greatly reduces the complexity of the device construction and the cost of the unit, at the same time improves the reliability of the device. The shown embodiment can fit into a small person's hand comfortably. The device may be further miniaturized to reduce the throw-away waste as it is a fully disposable device. The main components of the embodiment shown in FIG. 1C were produced with off-the-shelf materials through a Computer Numeric Control (CNC, which is also commonly known as Computer Navigated Cutting) process. In other embodiments, production of the device employs the use of castings and/or moulds as appropriate to support high volume production. The power source of the device uses the disposable type of battery and is also fully integrated into the device. Both the simplified design of the device and high volume production process (such injection molding) make the device very cost-effective and enable the integrated device to be fully disposable.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description has been presented for purposes of illustration and description, but is not intended to be exhaustive or limited to the form disclosed. Many modifications and variations will be apparent to those of ordinary skill in the art without departing from the scope of the claims. The embodiment was chosen and described in order to best explain the principles of the technology and the practical application, and to enable others of ordinary skill in the art to understand the technology for various embodiments with various modifications as are suited to the particular use contemplated.

One or more currently preferred embodiments have been described by way of example. It will be apparent to persons skilled in the art that a number of variations and modifications can be made without departing from the scope of the claims.

---

What is claimed is:

1. A fully integrated, stand-alone point-of-care device for detecting a target nucleic acid sequence comprising:

an extraction and amplification chamber adapted to receive a biological sample for extracting and lysing the sample to release nucleic acid and for receiving amplification reagents for amplifying one or more target nucleic acid sequences;

the extraction and amplification chamber having an opening and sized to receive a head of a swab carrying a biological sample into the extraction and amplification chamber, wherein the extraction and amplification chamber comprise a pouch containing a lysis solution for extracting and lysing the biological sample to release nucleic acid;

a heater connected to the extraction and amplification chamber for extraction and lysis of nucleic acid from the biological sample;

a detection element within the extraction and amplification chamber, wherein the detection element comprises a detection surface that is at least a portion of a wall of the extraction and amplification chamber that is coated with a plurality of distinct capture probes for capturing the amplified target nucleic acid, wherein each distinct capture probe is coated onto different locations of the detection surface and adapted to capture an amplified target nucleic acid segment from a different pathogen, for detection of multiple target nucleic acids in a single chamber;

a reading area for displaying a detectable signal associated with the captured and amplified target nucleic acid segments when a detection agent is introduced, wherein the reading area is positioned to correspond to the different locations of the detection surface coated with the plurality of distinct capture probes; and a lid for sealing the opening, wherein closure of the lid activates the heater to heat the extraction and amplification chamber, wherein insertion of the swab into the extraction chamber of the closure of the lid pierces the pouch exposing the head of the swab to the lysis solution.

2. The device of claim 1 wherein the extraction and amplification chamber is preloaded with a lysis solution.

3. The device of claim 1 wherein the extraction and amplification chamber is fluidly connected to a chamber containing a lysis solution, which is released upon receipt of a biological sample into the extraction chamber.

4. The device of claim 1 further comprising a motor used to facilitate mechanical lysis in the extraction and amplification chamber.

5. The device of claim 1 further comprising a waste fluid reservoir fluidly connected to the extraction and amplification chamber.

6. The device of claim 1, wherein the extraction and amplification chamber is connected to at least one washing fluid chamber.

7. The device of claim 1 further comprising a primer storage chamber fluidly connected to the extraction and amplification chamber.

8. The device of claim 7, wherein the primer storage chamber comprises an amplification mixture comprising oligonucleotide primers to be introduced to the amplification chamber for amplification of the target nucleic acid sequence, a DNA polymerase, deoxynucleoside triphosphates, buffer and magnesium.

9. The device of claim 8, wherein the primers comprise detectable labels for detectably labelling the target nucleic acid.

10. The device of claim 9, wherein the detectable signal is produced by a detectable label selected from the group consisting of fluorescent labels, chemiluminescent labels, chromogenic labels, and electrochemically detectable labels.

11. The device of claim 1, wherein the device comprises a control chamber in communication with the extraction and amplification chamber adapted to amplify a positive control nucleic acid sequence, wherein said control chamber receives or is preloaded with an amplification mixture comprising oligonucleotide primers complementary to a control nucleic acid sequence.

12. The device of claim 11, wherein the oligonucleotide primers are isothermal DNA amplification primers for amplifying specific pathogenic sequences.

13. The device of claim 1, wherein the detection surface is lined with the plurality of distinct capture probes comprising immobilized target-capture nucleic acid probes.

14. The device of claim 1, wherein a positively charged electric field is utilized within the extraction and amplification chamber or at the detection surface to accelerate binding of nucleic acid to the one or more capture probes.

15. The device of claim 1, wherein the heater is configured to maintain a temperature of 58° C. to 66° C. in the extraction and amplification chamber.

16. The device of claim 1, further comprising amplification reagents for multiple target nucleic acid sequences.

17. The device of claim 1 comprising amplification reagents for multiple target nucleic acid sequences, and wherein the detection element comprises a detection surface having distinct dye spots coated thereon, said dye spots being labelled with molecules specifically complementary to amplified target nucleic acid segments.

18. The device of claim 1, where electrochemical detection of DNA is accomplished using methylene blue DNA binding dye.

19. The device of claim 1, where DNA is detected using a lateral flow assay.

20. The device of claim 1, wherein the heater is a self-regulating heater for maintaining the temperature during extraction, lysis and/or amplification.

21. The device of claim 1, wherein the device is hand-held.

22. The device of claim 1, wherein the reading area comprises one or more viewing windows forming a part of the wall of the extraction and amplification chamber, and wherein an internal surface of the one or more windows is coated with the plurality of distinct capture probes.

23. The device of claim 22, comprising a plurality of viewing windows each coated with a different distinct capture probe.

24. The device of claim 22, wherein an external surface of the viewing window is covered by an opaque layer having apertures therein corresponding to the location of each distinct capture probe.

* * * * *

SEQUENCE LISTING

```
<160> NUMBER OF SEQ ID NOS: 72

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
aggatggggg ctgtaacc                                                 18

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ccagccattt gctccatagc                                               20

<210> SEQ ID NO 3
<211> LENGTH: 40
<212> TYPE: DNA
<213> ORGANISM: Artificial Sequence
<220> FEATURE:
<223> OTHER INFORMATION: Primer

<400> SEQUENCE: 3
tgagacctgt gctgggagtc aaggtggcat tggcctggta                         40

<210> SEQ ID NO 4
```

<211> LENGTH: 41
<212> TYPE: DNA
<213> ORGANISM: Artificial Sequence
<220> FEATURE:
<223> OTHER INFORMATION: Primer

<400> SEQUENCE: 4
taggcagatg gtggcaacaa cctgtagtgc tggccaaaac c        41

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
aatctgctca catgttgcac a        21

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
cattaataaa acatgagaac agaat        25

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
ccgttttact cgtgccgc        18

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
agacgctttg tccaaaatgc        20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tcacaagtgg cacacactag        20

<210> SEQ ID NO 10
<211> LENGTH: 40
<212> TYPE: DNA
<213> ORGANISM: Artificial Sequence
<220> FEATURE:
<223> OTHER INFORMATION: Primer

<400> SEQUENCE: 10

```
ccttggcccc atggaacgtt atggggaccc gaacaacatg        40
```

<210> SEQ ID NO 11
<211> LENGTH: 41
<212> TYPE: DNA
<213> ORGANISM: Artificial Sequence
<220> FEATURE:
<223> OTHER INFORMATION: Primer

<400> SEQUENCE: 11

```
ttcaactggt gcacttgcca gtgtggtcac tgttcccatc c      41
```

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12

```
tgagcttctt gtatagttta actgc                       25
```

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13

```
tgcatgggcc tcatatacaa ca                          22
```

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14

```
agggacatga acaacaaaga                             20
```

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15

```
caagtttagc aacaagcct                              19
```

<210> SEQ ID NO 16
<211> LENGTH: 49
<212> TYPE: DNA
<213> ORGANISM: Artificial Sequence
<220> FEATURE:
<223> OTHER INFORMATION: Primer

<400> SEQUENCE: 16

```
tcagggacaa tacattacgc atatcgataa aggaggaagt aaacactca    49
```

<210> SEQ ID NO 17
<211> LENGTH: 43
<212> TYPE: DNA

```
<213> ORGANISM: Artificial Sequence
<220> FEATURE:
<223> OTHER INFORMATION: Primer

<400> SEQUENCE: 17
taaacggaac attcctcaaa caccactctg gtcataggca ttc          43

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
tcaaacggaa cttcccttct ttc                                23

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
ggatacaagt ccttatcaac tctgc                              25

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
gctgttcaat acaatgtcct aga                                23

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
ggtaaatttg ctgggcatt                                     19

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
tctgctggca tggatgattg gagacgatga tcctgcatca              40

<210> SEQ ID NO 23
<211> LENGTH: 44
<212> TYPE: DNA
<213> ORGANISM: Artificial Sequence
<220> FEATURE:
<223> OTHER INFORMATION: Primer

<400> SEQUENCE: 23
ctagtgaaac aaatatccac acccagcact gcacttcttg agtt         44
```

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
acatgggcac catattgtaa g                                            21

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
agggaccttc attaagagtc atgat                                        25

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
aaccattcct gctacagat                                               19

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
catcttgagc atgatatttt gc                                           22

<210> SEQ ID NO 28
<211> LENGTH: 47
<212> TYPE: DNA
<213> ORGANISM: Artificial Sequence
<220> FEATURE:
<223> OTHER INFORMATION: Primer

<400> SEQUENCE: 28
agcatcgcag acaaagatac taatcaacta acaacataca ttggtct                47

<210> SEQ ID NO 29
<211> LENGTH: 43
<212> TYPE: DNA
<213> ORGANISM: Artificial Sequence
<220> FEATURE:
<223> OTHER INFORMATION: Primer

<400> SEQUENCE: 29
cctgtcacag ccaattggag tcagaagaac agtatttgca ctt                    43

<210> SEQ ID NO 30
<211> LENGTH: 38
<212> TYPE: DNA
<213> ORGANISM: Artificial Sequence
<220> FEATURE:

<223> OTHER INFORMATION: Primer

<400> SEQUENCE: 30
aacgccgtca acgacgtcgt gccctcgagg acctgctc                    38

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31
aggttctgca aatttatat gtaaata                                 27

<210> SEQ ID NO 32
<211> LENGTH: 19
<212> TYPE: DNA
<213> ORGANISM: Artificial Sequence
<220> FEATURE:
<223> OTHER INFORMATION: Primer

<400> SEQUENCE: 32
ttcaatgaca gtcccaact                                         19

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
ggtttccagt ccatcctg                                          18

<210> SEQ ID NO 34
<211> LENGTH: 48
<212> TYPE: DNA
<213> ORGANISM: Artificial Sequence
<220> FEATURE:
<223> OTHER INFORMATION: Primer

<400> SEQUENCE: 34
gcgtccttcc taactcatct aattttagg tactagtcag attactcc          48

<210> SEQ ID NO 35
<211> LENGTH: 45
<212> TYPE: DNA
<213> ORGANISM: Artificial Sequence
<220> FEATURE:
<223> OTHER INFORMATION: Primer

<400> SEQUENCE: 35
ctgctagagg tacattgact tatgccgggg ttttgatttt taccg            45

<210> SEQ ID NO 36
<211> LENGTH: 22
<212> TYPE: DNA
<213> ORGANISM: Artificial Sequence
<220> FEATURE:
<223> OTHER INFORMATION: Primer

<400> SEQUENCE: 36
tcctgcttta ggaaagagtg ct                                     22

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
caatgttgaa ggtagctacg gt                                              22

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
caaacctaac aatacacatg aaca                                            24

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
acgctaagcc acgtccatat                                                 20

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
cgttgtcttc gctccaaat                                                  19

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
tgcaaagaaa attgaagtcg a                                               21

<210> SEQ ID NO 42
<211> LENGTH: 42
<212> TYPE: DNA
<213> ORGANISM: Artificial Sequence
<220> FEATURE:
<223> OTHER INFORMATION: Primer

<400> SEQUENCE: 42
tcaaggcttg gctaaagttg cttattcgct tgtgcttcac tt                        42

<210> SEQ ID NO 43
<211> LENGTH: 46
<212> TYPE: DNA
<213> ORGANISM: Artificial Sequence
<220> FEATURE:
<223> OTHER INFORMATION: Primer

<400> SEQUENCE: 43
cgtttaccat ttttccatca gcatatttga caaaggtcaa agaact        46

<210> SEQ ID NO 44
<211> LENGTH: 10
<212> TYPE: DNA
<213> ORGANISM: Artificial Sequence
<220> FEATURE:
<223> OTHER INFORMATION: Primer

<400> SEQUENCE: 44
ctggcgatat        10

<210> SEQ ID NO 45
<211> LENGTH: 10
<212> TYPE: DNA
<213> ORGANISM: Artificial Sequence
<220> FEATURE:
<223> OTHER INFORMATION: Primer

<400> SEQUENCE: 45
atatcgccag        10

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46
atatcgccag gtgagactct atatcgccag        30

<210> SEQ ID NO 47
<211> LENGTH: 36
<212> TYPE: DNA
<213> ORGANISM: Artificial Sequence
<220> FEATURE:
<223> OTHER INFORMATION: Primer

<400> SEQUENCE: 47
ctggcgcttg atggtatcca gactctatat cgccag        36

<210> SEQ ID NO 48
<211> LENGTH: 38
<212> TYPE: DNA
<213> ORGANISM: Artificial Sequence
<220> FEATURE:
<223> OTHER INFORMATION: Primer

<400> SEQUENCE: 48
gagtccagta tttggtcgtc tgtcctgcgt agcgactc        38

<210> SEQ ID NO 49
<211> LENGTH: 29
<212> TYPE: DNA
<213> ORGANISM: Artificial Sequence
<220> FEATURE:
<223> OTHER INFORMATION: Primer

<400> SEQUENCE: 49
atttggtcgt cgcagactca tttggtcgt        29

<210> SEQ ID NO 50
<211> LENGTH: 43

-continued

```
<212> TYPE: DNA
<213> ORGANISM: Artificial Sequence
<220> FEATURE:
<223> OTHER INFORMATION: Primer

<400> SEQUENCE: 50
accgggcaga ttcggcccac ttcccgcaga ctcatttggt cgt                    43

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51 tttttttta ccgggcagat t                                             21

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
cggcccactt ccttttttt t                                             21

<210> SEQ ID NO 53
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: biotin-sp18 conjugate

<400> SEQUENCE: 53
aatctgcccg gtaaaa                                                  16

<210> SEQ ID NO 54
<211> LENGTH: 69
<212> TYPE: DNA
<213> ORGANISM: Artificial Sequence
<220> FEATURE:
<223> OTHER INFORMATION: Primer

<400> SEQUENCE: 54
tcaagagtag acacaggatc agcataggca atagatggag tcacgtaatc agatcagagc  60
aataggtca                                                          69

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
atggtagatg gttggtatgg gta                                          23

<210> SEQ ID NO 56
<211> LENGTH: 26
<212> TYPE: DNA
```

```
<213> ORGANISM: Artificial Sequence
<220> FEATURE:
<223> OTHER INFORMATION: Primer

<400> SEQUENCE: 56
cgtaggcaat agatggagtc actacg                                          26

<210> SEQ ID NO 57
<211> LENGTH: 56
<212> TYPE: DNA
<213> ORGANISM: Artificial Sequence
<220> FEATURE:
<223> OTHER INFORMATION: Primer

<400> SEQUENCE: 57
aattctaata cgactcacta tagggagaag gtgacctatt gctctgatct gattac         56

<210> SEQ ID NO 58
<211> LENGTH: 69
<212> TYPE: DNA
<213> ORGANISM: Artificial Sequence
<220> FEATURE:
<223> OTHER INFORMATION: Primer

<400> SEQUENCE: 58
taatacgact cactataggt gacctattgc tctgatctga ttactcaaga gtagacacag     60
gatcagcat                                                             69

<210> SEQ ID NO 59
<211> LENGTH: 56
<212> TYPE: DNA
<213> ORGANISM: Artificial Sequence
<220> FEATURE:
<223> OTHER INFORMATION: Primer

<400> SEQUENCE: 59
ggatgatctg aattttctca aacccggtca acttcaagct cctaagcctt gacgaa         56

<210> SEQ ID NO 60
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(20)
<223> OTHER INFORMATION: phosphorothioate modifications

<400> SEQUENCE: 60
gcttaggagc ttgaagttga c                                               21

<210> SEQ ID NO 61
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(20)
<223> OTHER INFORMATION: phosphorothioate modifications

<400> SEQUENCE: 61
gctttgcctg actgaatgca g                                               21
```

```
<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
cttttagggg tgttaggggt                                              20

<210> SEQ ID NO 63
<211> LENGTH: 24
<212> TYPE: DNA
<213> ORGANISM: Artificial Sequence
<220> FEATURE:
<223> OTHER INFORMATION: Primer

<400> SEQUENCE: 63
aagcttactt tctaacacta acgc                                         24

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
cgattgggga taagtttgtg                                              20

<210> SEQ ID NO 65
<211> LENGTH: 35
<212> TYPE: DNA
<213> ORGANISM: Artificial Sequence
<220> FEATURE:
<223> OTHER INFORMATION: Primer

<400> SEQUENCE: 65
tccaacatga agatggctat cgtgtcacaa tcgtt                             35

<210> SEQ ID NO 66
<211> LENGTH: 32
<212> TYPE: DNA
<213> ORGANISM: Artificial Sequence
<220> FEATURE:
<223> OTHER INFORMATION: Primer

<400> SEQUENCE: 66
cctgtttgag ggtggatagc agtacctgag cc                                32

<210> SEQ ID NO 67
<211> LENGTH: 34
<212> TYPE: DNA
<213> ORGANISM: Artificial Sequence
<220> FEATURE:
<223> OTHER INFORMATION: Primer

<400> SEQUENCE: 67
taccgggcat accatccaga gaaaatcggg ccgc                              34

<210> SEQ ID NO 68
<211> LENGTH: 32
<212> TYPE: DNA
<213> ORGANISM: Artificial Sequence
<220> FEATURE:
<223> OTHER INFORMATION: Primer
```

```
<400> SEQUENCE: 68
attggcgata gcctggcggt gggttttgtt gt                                32

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
aacatcactg ttactggtta c                                           21

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
ctgctattgt atttattatc tacgc                                       25

<210> SEQ ID NO 71
<211> LENGTH: 43
<212> TYPE: DNA
<213> ORGANISM: Artificial Sequence
<220> FEATURE:
<223> OTHER INFORMATION: Primer

<400> SEQUENCE: 71
ctcgccacca atatagacaa cttttggtga caaaccatta gcc                   43

<210> SEQ ID NO 72
<211> LENGTH: 50
<212> TYPE: DNA
<213> ORGANISM: Artificial Sequence
<220> FEATURE:
<223> OTHER INFORMATION: Primer

<400> SEQUENCE: 72
gacctaagta ctgtaggtgg aaactcacca taatgtattc caataacttg            50
```